(12) United States Patent
Nakai et al.

(10) Patent No.: US 12,075,976 B2
(45) Date of Patent: *Sep. 3, 2024

(54) FLEXIBLE TUBE FOR ENDOSCOPE, ENDOSCOPIC MEDICAL DEVICE, AND METHODS FOR PRODUCING THE SAME

(71) Applicant: FUJIFILM Corporation, Tokyo (JP)

(72) Inventors: Yoshihiro Nakai, Ashigarakami-gun (JP); Toshihide Yoshitani, Ashigarakami-gun (JP); Shinya Abe, Ashigarakami-gun (JP); Kazuma Horita, Ashigarakami-gun (JP); Takeshi Senga, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 534 days.

This patent is subject to a terminal disclaimer.

(21) Appl. No.: 17/343,899

(22) Filed: Jun. 10, 2021

(65) Prior Publication Data

US 2021/0298564 A1  Sep. 30, 2021

Related U.S. Application Data

(63) Continuation of application No. PCT/JP2020/000876, filed on Jan. 14, 2020.

(30) Foreign Application Priority Data

Jan. 16, 2019 (JP) ................................ 2019-005384

(51) Int. Cl.
*A61B 1/005* (2006.01)
*A61L 29/08* (2006.01)
(Continued)

(52) U.S. Cl.
CPC ............ *A61B 1/005* (2013.01); *A61L 29/085* (2013.01); *B29C 48/10* (2019.02); *B29C 48/151* (2019.02);
(Continued)

(58) Field of Classification Search
CPC ... A61B 1/005; A61B 1/0011; A61B 1/00135; A61L 29/085; A61L 29/02;
(Continued)

(56) References Cited

U.S. PATENT DOCUMENTS

| 6,083,152 A | 7/2000 | Strong |
| 2011/0245612 A1 | 10/2011 | Nakamura |
| 2016/0088998 A1 | 3/2016 | Nagai et al. |

FOREIGN PATENT DOCUMENTS

| JP | 59-154417 A | 9/1984 |
| JP | 5-220102 A | 8/1993 |

(Continued)

OTHER PUBLICATIONS

Shin-Etsu Chemical Co., Ltd, "Silane Coupling Agents", 2017, retrieved online URL:<https//www.silicone.jp/catalog/pdf/SilaneCouplingAgents_J.pdf>, pp. 1-28 (28 pages total).
(Continued)

*Primary Examiner* — James C Yager
(74) *Attorney, Agent, or Firm* — Sughrue Mion, PLLC

(57) ABSTRACT

Provided are a flexible tube for an endoscope, the flexible tube having a flexible tube base containing metal as a constituent material, a resin cover layer that covers an outer periphery of the flexible tube base, and a primer layer that includes a specific silane coupling agent and that is disposed between the flexible tube base and the resin cover layer, in which the resin cover layer includes at least one compound selected from the group consisting of polyamides, polyesters, polyurethanes, and polyolefins at least on a side of the resin cover layer in contact with the primer layer, an endoscopic medical device including the flexible tube for an endoscope, a method for producing the flexible tube for an endoscope, and a method for producing the endoscopic medical device.

18 Claims, 4 Drawing Sheets

(51) Int. Cl.
    *B29C 48/10*     (2019.01)
    *B29C 48/151*     (2019.01)
    *B32B 1/08*     (2006.01)
    *B32B 15/08*     (2006.01)
    *B32B 27/08*     (2006.01)
    *A61L 29/02*     (2006.01)
    *B29K 101/12*     (2006.01)
    *B29K 705/12*     (2006.01)
    *B29L 31/00*     (2006.01)
    *B32B 15/18*     (2006.01)

(52) U.S. Cl.
    CPC ................ *B32B 1/08* (2013.01); *B32B 15/08* (2013.01); *B32B 27/08* (2013.01); *A61L 29/02* (2013.01); *A61L 2420/08* (2013.01); *B29K 2101/12* (2013.01); *B29K 2705/12* (2013.01); *B29L 2031/753* (2013.01); *B32B 15/18* (2013.01); *B32B 2535/00* (2013.01); *Y10T 428/1393* (2015.01)

(58) Field of Classification Search
    CPC ... A61L 2420/08; B29C 48/10; B29C 48/151; B29C 48/21; B29C 48/338; B29C 2948/9259; B29C 2948/926; B29C 2948/92847; B29C 2948/92866; B29C 2948/92933; B32B 1/08; B32B 15/08; B32B 27/08; B32B 15/18; B32B 2535/00; B29K 2101/12; B29K 2705/12; B29L 2031/753; Y10T 428/1393; G02B 23/24; C08L 67/00; C08L 75/04; C08L 77/00; C08L 23/00; C08L 77/12
    See application file for complete search history.

(56) References Cited

FOREIGN PATENT DOCUMENTS

| | | |
|---|---|---|
| JP | 2011-212338 A | 10/2011 |
| JP | 2016-67566 A | 5/2016 |

OTHER PUBLICATIONS

International Preliminary Report on Patentability dated Jun. 16, 2021 in Application No. PCT/JP2020/000876.
International Search Report dated Mar. 24, 2020 with translation of the Written Opinion in Application No. PCT/JP2020/000876.
Written Opinion of the International Searching Authority dated Mar. 24, 2020 in Application No. PCT/JP2020/000876.

FLEXIBLE TUBE FOR ENDOSCOPE, ENDOSCOPIC MEDICAL DEVICE, AND METHODS FOR PRODUCING THE SAME

CROSS-REFERENCE TO RELATED APPLICATIONS

This application is a Continuation of PCT International Application No. PCT/JP2020/000876 filed on Jan. 14, 2020, which claims priority under 35 U.S.C. § 119 (a) to Japanese Patent Application No. 2019-005384 filed in Japan on Jan. 16, 2019. Each of the above applications is hereby expressly incorporated by reference, in its entirety, into the present application.

BACKGROUND OF THE INVENTION

1. Field of the Invention

The present invention relates to a flexible tube for an endoscope, an endoscopic medical device, and methods for producing the same.

2. Description of the Related Art

Endoscopes are medical devices for examining the inside of the body cavity, the inside of the digestive tract, the esophagus, or the like of a patient. Since endoscopes are inserted and used in the body, it is desirable to provide endoscopes that do not damage organs or cause pain or discomfort to a patient. In view of such a requirement, a spiral tube formed by winding a soft, bendable metal strip in a spiral form is adopted as a flexible tube that forms an insertion section (structural section to be inserted into a body cavity) of an endoscope. Furthermore, the periphery of the spiral tube is covered with a flexible resin, and this resin cover layer is covered with a topcoat layer, as needed, so that the spiral tube does not cause stimulation or damage to an inner surface of, for example, the esophagus, digestive tract, or body cavity.

The resin cover layer can be formed by, for example, extrusion-molding a resin on an outer peripheral surface of a flexible tube base that is formed by covering a spiral tube with a tubular mesh. In this case, it is preferable to make the distal end side soft so as to easily insert the flexible tube into the body cavity and to make the proximal end side hard so as to easily perform the operation. In consideration of this point, it has been proposed that a two-layer structure having an inner layer and an outer layer that have different degrees of hardness is adopted as the resin cover layer, and a ratio of the thickness of the inner layer to the thickness of the outer layer is changed in the axial direction of the flexible tube.

To improve operability, durability, and the like of an endoscope, it is important to enhance adhesiveness between a flexible tube base and a resin cover layer that covers the flexible tube base. If this adhesiveness is insufficient, when a flexible tube is inserted into a body cavity, for example, a crease, floating, tearing, or separation is easily caused on the resin cover layer by bending of the flexible tube. In addition, when the flexible tube is rotated in the body cavity, twisting of the resin cover layer tends to occur. If such a crease, floating, tearing, separation, or twisting is caused in the resin cover layer, for example, the surface of the flexible tube catches the inside of the body cavity, which may cause a pain to a subject. Furthermore, when the flexible tube is inserted into a body cavity, the flexible tube is exposed to a body fluid. For example, in gastroendoscopy, the flexible tube is exposed to the gastric juice including hydrochloric acid. Therefore, the flexible tube is required to be capable of maintaining adhesiveness between the flexible tube base and the resin cover layer even when repeatedly exposed to a strong acid.

It is known that a primer layer is disposed between the flexible tube base and the resin cover layer to increase the adhesiveness. For example, JP2011-212338A discloses that a primer is applied to a surface of a metal core (flexible tube base) and an outer coating layer is then formed so as to cover the primer and that a silane coupling agent, a titanate coupling agent, a zirconate coupling agent, or the like can be used as the primer.

SUMMARY OF THE INVENTION

An object of the present invention is to provide a flexible tube for an endoscope, the flexible tube being capable of sufficiently maintaining adhesiveness between a flexible tube base and a resin cover layer that covers the flexible tube base even when a bending operation is repeated and being less likely to undergo a decrease in the adhesiveness between the flexible tube base and the resin cover layer even when the flexible tube is immersed in a strongly acidic liquid (e.g., gastric juice) and to provide an endoscopic medical device that includes the flexible tube for an endoscope. Another object of the present invention is to provide a method for producing the flexible tube for an endoscope and a method for producing the endoscopic medical device.

The inventors of the present invention have conducted extensive studies on formation of a resin cover layer in a flexible tube for an endoscope. As a result, the inventors have found that the above objects can be achieved by forming a primer layer that includes a silane coupling agent with a specific structure on a surface of a flexible tube base formed of a metal material, and using a specific polymer as a constituent material of a resin cover layer that is in contact with the primer layer. The inventors have further conducted studies on the basis of these findings and completed the present invention.

The objects of the present invention have been achieved by the following means.

<1>

A flexible tube for an endoscope, the flexible tube having a flexible tube base containing metal as a constituent material; a resin cover layer that covers an outer periphery of the flexible tube base; and a primer layer that includes a compound represented by general formula (1) and that is disposed between the flexible tube base and the resin cover layer, in which the resin cover layer includes at least one compound selected from the group consisting of polyamides, polyesters, polyurethanes, and polyolefins at least on a side of the resin cover layer in contact with the primer layer.

$$LL^1 \!-\!\!\left(\!L^1\!-\!\!\underset{\underset{Y^3}{|}}{\overset{\overset{Y^1}{|}}{Si}}\!-\!Y^2\right)_{\!n1} \quad \text{General formula (1)}$$

In the formula, $LL^1$ represents a monovalent substituent or an n1-valent linking group, $L^1$ represents a single bond or a divalent linking group, $Y^1$ to $Y^3$ each represent a substituent, and n1 is an integer of 1 to 4.

At least one of $Y^1$, $Y^2$, or $Y^3$ is a group selected from the group consisting of alkoxy groups and a hydroxy group. When n1 is 1, none of $LL^1$-$L^1$ and $Y^1$ to $Y^3$ is a group selected from the group consisting of alkoxy groups and a hydroxy group.

<2>

The flexible tube for an endoscope according to <1>, in which the compound represented by general formula (1) is a compound represented by any one of general formulae (2) to (4).

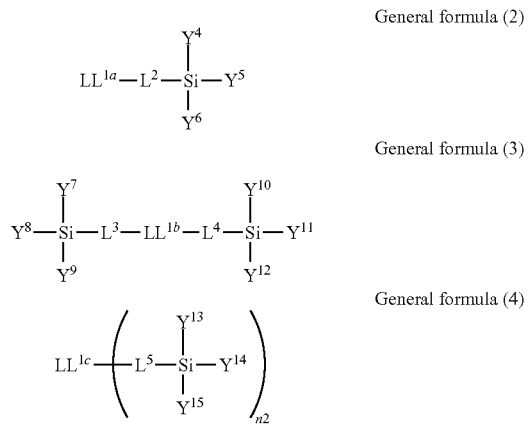

General formula (2)

General formula (3)

General formula (4)

In the formula, $LL^{1a}$ represents a hydrogen atom, an alicyclic group, a heterocyclic group, a hydroxy group, a sulfanyl group, an isocyanato group, a thiocyanato group, an ureido group, a cyano group, an acid anhydride group, an azide group, a carboxy group, an acyl group, a thiocarbamoyl group, a phosphate group, a phosphanyl group, a sulfonic group, or a sulfamoyl group.

$L^2$ represents a single bond, an alkylene group, an alkenylene group, an alkynylene group, an arylene group, —O—, —S—, —$NR^a$—, an ester bond, a thioester bond, an amide bond, a thioamide bond, a sulfonyl group, or a divalent group which is a combination of two or more selected from the group consisting of the aforementioned groups and bonds.

$L^3$ to $L^5$ each represent a single bond, an alkylene group, an alkenylene group, an alkynylene group, an arylene group, —O—, —S—, —$NR^a$—, an ester bond, a thioester bond, an amide bond, a thioamide bond, a urea bond, a thiourea bond, a sulfonyl group, a sulfonamide bond, or a divalent group which is a combination of two or more selected from the group consisting of the aforementioned groups and bonds.

$LL^{1b}$ represents a single bond, an alkylene group, an alkenylene group, an alkynylene group, an arylene group, —O—, —S—, —$NR^a$—, a divalent heterocyclic group, an amide bond, an ester bond, a thioester bond, a divalent phosphate group, a phosphanediyl group, a sulfonyl group, or a divalent group which is a combination of two or more selected from the group consisting of the aforementioned groups and bonds.

$LL^{1c}$ represents an n2-valent alkane, an n2-valent alkene, an n2-valent alkyne, an n2-valent arene, an n2-valent heterocyclic group, a trivalent phosphate group, a phosphanetriyl group, an isocyanurate group, or an n2-valent group which is a combination of two or more groups and bonds selected from the group consisting of the aforementioned groups, alkylene a thioester bond, an amide bond, a thioamide bond, and a sulfonyl group.

$R^a$ represents a hydrogen atom or a substituent.

$Y^4$, $Y^7$, $Y^{10}$, and $Y^{13}$ each represent a hydroxy group or an alkoxy group. $Y^5$, $Y^6$, $Y^8$, $Y^9$, $Y^{11}$, $Y^{12}$, $Y^{14}$, and $Y^{15}$ each represent a hydroxy group, an alkoxy group, an alkyl group, or a ketoxime group.

n2 is 3 or 4.

<3>

The flexible tube for an endoscope according to <2>, in which, in general formula (2),
$LL^{1a}$ represents a hydrogen atom, an alicyclic group, a heterocyclic group, a hydroxy group, a sulfanyl group, a thiocyanato group, an acid anhydride group, a carboxy group, an acyl group, or a sulfonic group, and
$L^2$ represents an alkylene group, an alkenylene group, an alkynylene group, an arylene group, —O—, —S—, —$NR^a$—, an ester bond, a thioester bond, an amide bond, a sulfonyl group, or a divalent group which is a combination of two or more selected from the group consisting of the aforementioned groups and bonds.

<4>

The flexible tube for an endoscope according to <2> or <3>,
in which, in general formula (2),
$LL^{1a}$ represents a hydrogen atom, a hydroxy group, a carboxylic acid anhydride group, a carboxy group, an acyl group, or a sulfonic group, and
$L^2$ represents an alkylene group, an alkenylene group, —O—, —$NR^a$—, an ester bond, an amide bond, or a divalent group which is a combination of two or more selected from the group consisting of the aforementioned groups and bonds.

<5>

The flexible tube for an endoscope according to any one of <2> to <4>,
in which, in general formula (3),
$LL^{1b}$ represents an alkylene group, an alkenylene group, an arylene group, —O—, —S—, an ester bond, a thioester bond, an amide bond, a sulfonyl bond, or a divalent group which is a combination of two or more selected from the group consisting of the aforementioned groups and bonds, and
$L^3$ and $L^4$ each represent a single bond, an alkylene group, an alkenylene group, an alkynylene group, an arylene group, —O—, —S—, an ester bond, a thioester bond, an amide bond, a sulfonyl group, or a divalent group which is a combination of two or more selected from the group consisting of the aforementioned groups and bonds.

<6>

The flexible tube for an endoscope according to any one of <2> to <5>,
in which, in general formula (3),
$LL^{1b}$ represents an alkylene group, an alkenylene group, an arylene group, —O—, —S—, an ester bond, a thioester bond, an amide bond, a sulfonyl bond, or a divalent group which is a combination of two or more selected from the group consisting of the aforementioned groups and bonds, and
$L^3$ and $L^4$ each represent a single bond, an alkylene group, an alkenylene group, —O—, an ester bond, or an amide bond.

<7>
The flexible tube for an endoscope according to any one of <2> to <6>,
in which, in general formula (4), n2 is 3, $LL^{1c}$ represents an isocyanurate group, and $L^5$ represents an alkylene group.
<8>
The flexible tube for an endoscope according to any one of <1> to <7>, in which the metal that constitutes the flexible tube base is stainless steel.
<9>
The flexible tube for an endoscope according to any one of <1> to <8>, in which the metal that constitutes the flexible tube base has a passivation film on a surface thereof.
<10>
The flexible tube for an endoscope according to any one of <1> to <9>, in which the resin cover layer has a single-layer structure or a multilayer structure and includes at least one compound selected from the group consisting of polyamides, polyesters, polyurethanes, and polyolefins in a layer in contact with the primer layer.
<11>
The flexible tube for an endoscope according to any one of <1> to <10>, in which the resin cover layer includes at least one compound selected from the group consisting of polyamides, polyesters, and polyurethanes at least on the side of the resin cover layer in contact with the primer layer.
<12>
The flexible tube for an endoscope according to any one of <1> to <11>, in which the resin cover layer has a two-layer structure, and a ratio of a thickness of an inner layer to a thickness of an outer layer of the two-layer structure changes in a gradient manner in an axial direction of the flexible tube base.
<13>
The flexible tube for an endoscope according to <12>, in which the ratio of the thickness of the inner layer to the thickness of the outer layer is inner layer:outer layer=95:5 to 60:40 at one end of the flexible tube for an endoscope and is inner layer:outer layer=5:95 to 40:60 at the other end.
<14>
An endoscopic medical device having the flexible tube for an endoscope according to any one of <1> to <13>.
<15>
A method for producing a flexible tube for an endoscope, the method including:
a step of forming, on at least an outer periphery of a flexible tube base that contains metal as a constituent material, a primer layer that includes a compound represented by general formula (1); and
a step of forming a resin cover layer by covering, with a resin that includes at least one compound selected from the group consisting of polyamides, polyesters, polyurethanes, and polyolefins, the primer layer formed on the outer periphery of the flexible tube base so as to be in contact with the primer layer.

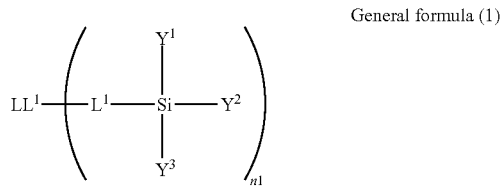

General formula (1)

In the formula, $LL^1$ represents a monovalent substituent or an n1-valent linking group, $L^1$ represents a single bond or a divalent linking group, $Y^1$ to $Y^3$ each represent a substituent, and n1 is an integer of 1 to 4.
At least one of $Y^1$, $Y^2$, or $Y^3$ is a group selected from the group consisting of alkoxy groups and a hydroxy group. When n1 is 1, none of $LL^1$-$L^1$ and $Y^1$ to $Y^3$ is a group selected from the group consisting of alkoxy groups and a hydroxy group.
<16>
The method for producing a flexible tube for an endoscope according to <15>, in which the resin cover layer has a two-layer structure, at least an inner layer of the two-layer structure includes at least one compound selected from the group consisting of polyamides, polyesters, polyurethanes, and polyolefins, and a ratio of a thickness of the inner layer to a thickness of an outer layer of the two-layer structure changes in a gradient manner in an axial direction of the flexible tube base.
<17>
A method for producing an endoscopic medical device, including:
a step of producing a flexible tube for an endoscope by the method for producing a flexible tube for an endoscope according to <15> or <16>; and
a step of incorporating the produced flexible tube for an endoscope into an insertion section of an endoscopic medical device.
<18>
A method for producing an endoscopic medical device, including incorporating the flexible tube for an endoscope according to any one of <1> to <13> into an insertion section of an endoscopic medical device.

In the present invention, when a plurality of substituents, linking groups, or the like (hereinafter referred to as substituents or the like) represented by specific symbols are present or a plurality of substituents or the like are defined simultaneously or alternatively, the substituents or the like may be the same or different from each other. In addition, even if not specifically stated, when a plurality of substituents or the like are adjacent to each other, they may be linked or fused to each other to form a ring.

In the present invention, the term "group" of each group described as an example of a substituent is meant to include both an unsubstituted form and a form having a substituent. For example, the term "alkyl group" means an alkyl group which may have a substituent. When the number of carbon atoms of a group is specified, the number of carbon atoms of this group means the total number of carbon atoms including a substituent, unless otherwise noted.

In the present invention, the designations of compounds are meant to include the compounds themselves, salts thereof, and ions thereof. These designations are also meant to include derivatives formed by changing a part of the structure within the range in which the effects of the present invention are not impaired. Furthermore, if it is not explicitly specified whether a compound is substituted or unsubstituted, it is meant that the compound may have any substituent within the range in which the effects of the present invention are not impaired. This also applies to substituents and linking groups.

In the present invention, the term "(meth)acrylate" is meant to include one or both of acrylate and methacrylate. This also applies to "(meth)acrylic acid", "(meth)acrylamide", "(meth)acrylonitrile", and "(meth)acryloyl group".

In the present invention, any numerical range expressed by using the word "to" means a range including the numerical values before and after the word "to" as the lower and upper limits thereof.

The flexible tube for an endoscope according to the present invention is capable of sufficiently maintaining adhesiveness between a flexible tube base and a resin cover layer that covers the flexible tube base even when a bending operation is repeated, is less likely to undergo a decrease in the adhesiveness between the flexible tube base and the resin cover layer even when the flexible tube is immersed in a strongly acidic liquid (e.g., gastric juice), and has good bending durability and good durability against strongly acidic liquids.

According to the endoscopic medical device according to the present invention, a flexible tube which is a structural section to be inserted into a body cavity has good bending durability and good durability against strongly acidic liquids. Therefore, in the endoscopic medical device according to the present invention, the load on a subject during use can be further reduced.

The method for producing a flexible tube for an endoscope according to the present invention can provide a flexible tube for an endoscope, the flexible tube having good bending durability and good durability against strongly acidic liquids.

According to the method for producing an endoscopic medical device according to the present invention, a flexible tube that forms this device can have good bending durability and good durability against strongly acidic liquids. Therefore, the method for producing an endoscopic medical device according to the present invention can provide an endoscopic medical device in which the load on a subject during use is further reduced.

DESCRIPTION OF THE PREFERRED EMBODIMENTS

Figure 1:
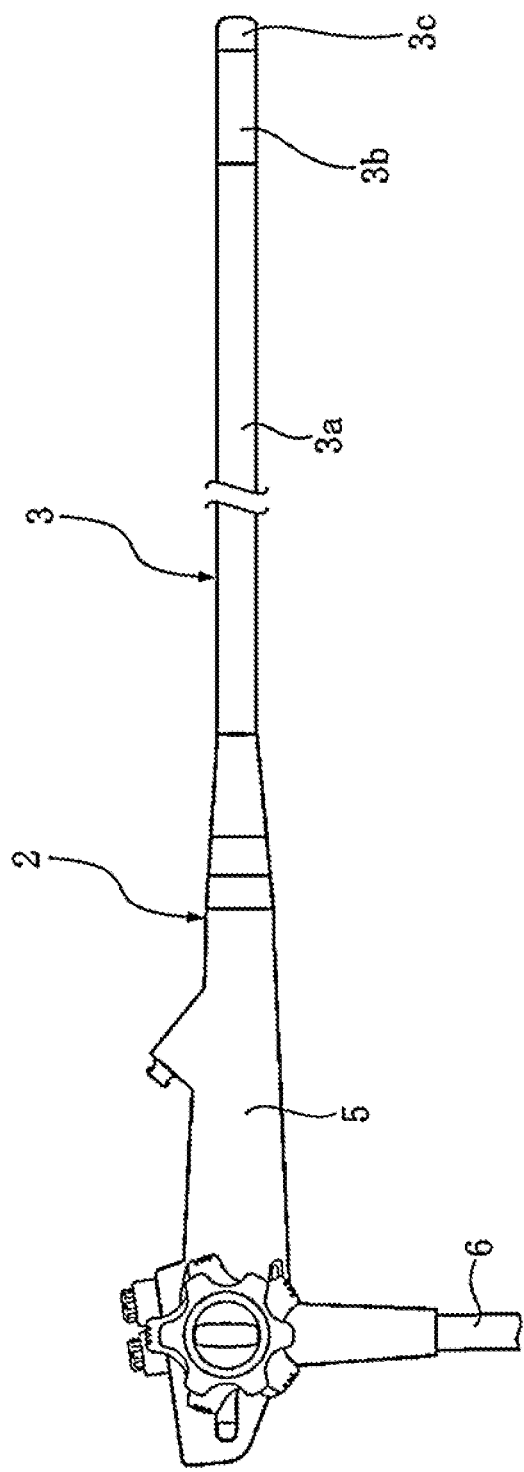
FIG. 1 is an external view illustrating a configuration of an electronic endoscope according to an embodiment.

An electronic endoscope will now be described as an example of an endoscopic medical device according to a preferred embodiment of the present invention. An electronic endoscope includes a flexible tube for an endoscope (hereinafter, a flexible tube for an endoscope may be simply referred to as a "flexible tube"), the flexible tube being incorporated in the electronic endoscope, and is used as a medical device for, for example, examining the inside of the body by inserting the flexible tube into the inside of the body cavity, the inside of the digestive tract, the esophagus, or the like. In the example illustrated in FIG. 1, an electronic endoscope 2 includes an insertion section 3 to be inserted into a body cavity, a main body operating section 5 that is connected to a proximal end portion of the insertion section 3, and a universal cord 6 to be connected to a processor device or a light source device. The insertion section 3 includes a flexible tube 3a connected to the main body operating section 5, an angle portion 3b connected to the flexible tube 3a, and a tip portion 3c which is connected to the distal end of the angle portion 3b and in which an imaging device (not shown) for imaging the inside of the body is installed. The flexible tube 3a that accounts for a large portion of the length of the insertion section 3 has flexibility across substantially the entire length thereof and is configured so that, in particular, a portion to be inserted into the inside of a body cavity or the like has higher flexibility.

Flexible Tube Base

The flexible tube has, as an innermost layer, a flexible tube base containing metal as a constituent material.

Figure 2:
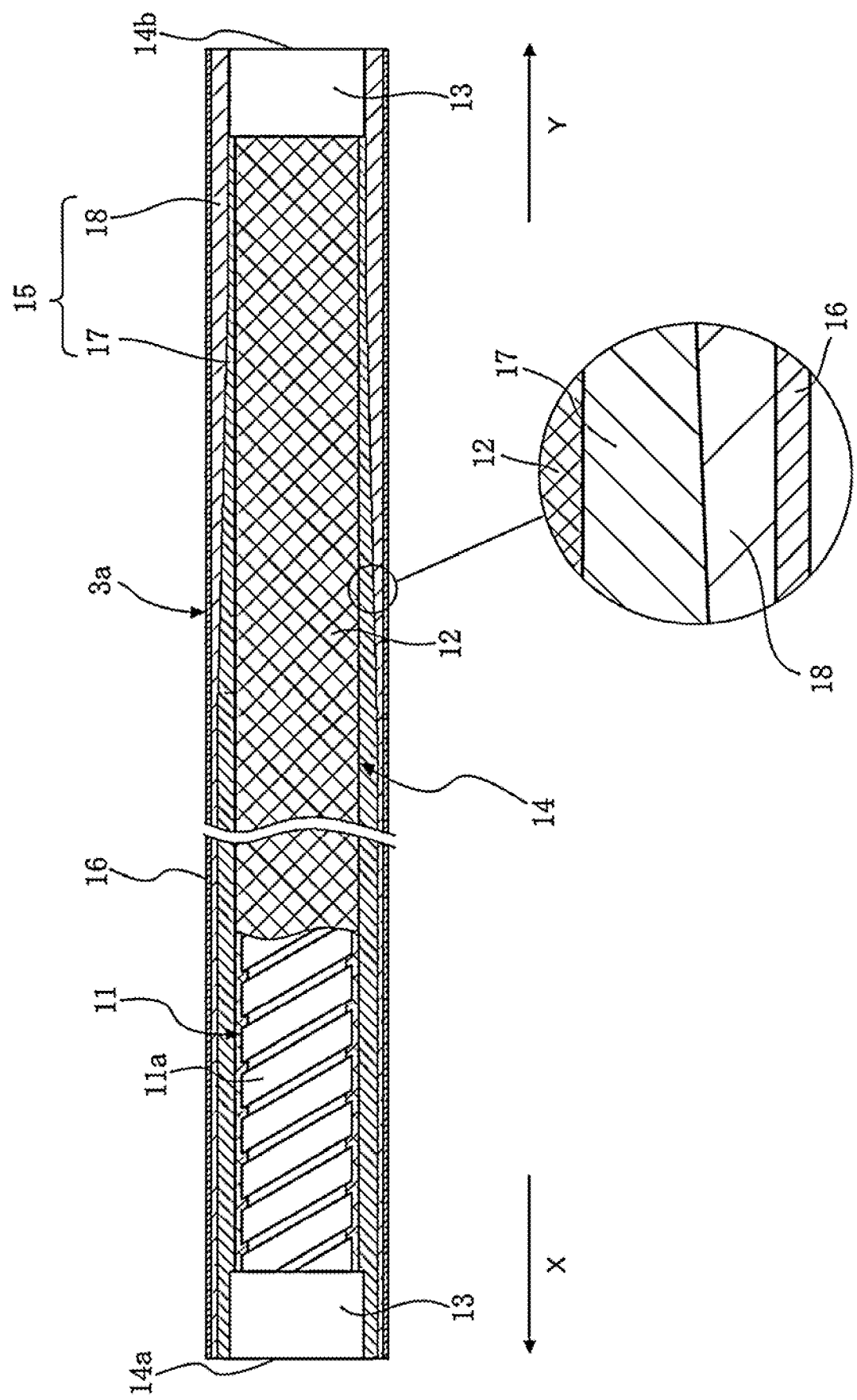
FIG. 2 is a partial sectional view illustrating a configuration of a flexible tube for an endoscope according to an embodiment.

As illustrated in FIG. 2, a flexible tube base 14 preferably has a form in which a spiral tube 11 that is formed, on the innermost side, by winding a metal strip 11a in a spiral form is covered with a tubular mesh 12 obtained by braiding metal wires, and caps 13 are fitted in both ends of the resulting product. The metal constituting the flexible tube base 14 preferably has a surface that has been subjected to passivation treatment in order to prevent corrosion. That is, the flexible tube base 14 preferably has a passivation film on an outer periphery (surface) thereof. This passivation treatment can be performed by an ordinary method. A passivation film can be formed on a surface of metal by, for example, immersing the metal in a solution including a strong oxidizing agent such as nitric acid, heating the metal in air (oxygen) or water (water vapor), or anodizing the metal in a solution including an oxidizing agent.

The metal that constitutes the flexible tube base 14 is preferably stainless steel. The surface of stainless steel is usually in a state in which chromium and oxygen ($O_2$) are bound to each other to form a passivation film. However, even in the case where stainless steel is used as the constituent material of the flexible tube base 14, the stainless steel is preferably subjected to the passivation treatment described above so that a more uniform passivation film is more reliably formed over the entire surface of the stainless steel.

Primer Layer

In the present invention, a primer layer (not shown) is disposed on an outer periphery of the flexible tube base. By disposing this primer layer, it is possible to enhance bending durability of the flexible tube for an endoscope and durability of the flexible tube against strongly acidic liquids. In the present invention, this primer layer includes a compound represented by general formula (1) below.

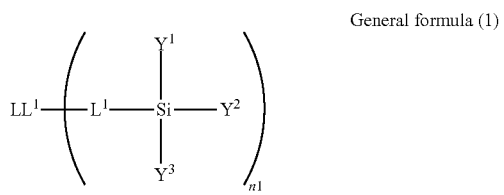

General formula (1)

In the formula, $LL^1$ represents a monovalent substituent or an n1-valent linking group, $L^1$ represents a single bond or a divalent linking group, $Y^1$ to $Y^3$ each represent a substituent, and n1 is an integer of 1 to 4 ($LL^1$ represents a monovalent substituent when n1 is 1, and $LL^1$ represents a divalent to tetravalent linking group when n1 is an integer of 2 to 4).

At least one of $Y^1$, $Y^2$, or $Y^3$ is a group selected from the group consisting of alkoxy groups and a hydroxy group.

When n1 is 1, none of $LL^1$-$L^1$ and $Y^1$ to $Y^3$ is a group selected from the group consisting of alkoxy groups and a hydroxy group.

The compound represented by general formula (1) above is preferably a compound represented by any one of general formulae (2) to (4) below and is more preferably a compound represented by general formula (3) or (4) below from the viewpoint of bending durability of the flexible tube for an endoscope and strong acidity.

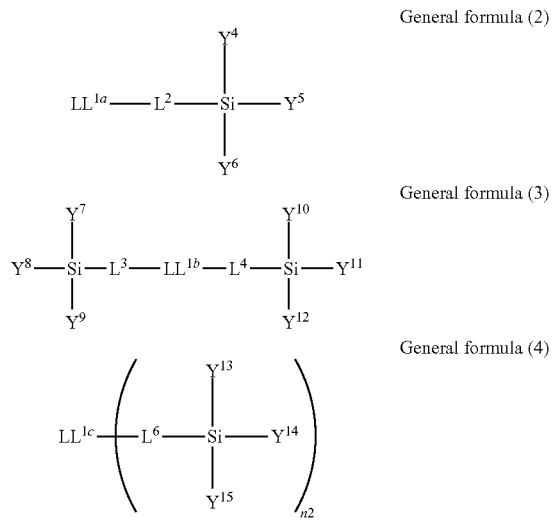

General formula (2)

General formula (3)

General formula (4)

In the formula, $LL^{1a}$ represents a hydrogen atom, an alicyclic group, a heterocyclic group, a hydroxy group, a sulfanyl group, an isocyanato group, a thiocyanato group, an ureido group, a cyano group, an acid anhydride group, an azide group, a carboxy group, an acyl group, a thiocarbamoyl group, a phosphate group, a phosphanyl group, a sulfonic group, or a sulfamoyl group.

$L^2$ represents a single bond, an alkylene group, an alkenylene group, an alkynylene group, an arylene group, —O—, —S—, —$NR^a$—, an ester bond, a thioester bond, an amide bond, a thioamide bond, a sulfonyl group, or a divalent group which is a combination of two or more selected from the group consisting of the aforementioned groups and bonds.

$L^3$ to $L'$ each represent a single bond, an alkylene group, an alkenylene group, an alkynylene group, an arylene group, —O—, —S—, —$NR^a$—, an ester bond, a thioester bond, an amide bond, a thioamide bond, a urea bond, a thiourea bond, a sulfonyl group, a sulfonamide bond, or a divalent group which is a combination of two or more selected from the group consisting of the aforementioned groups and bonds.

$LL^{1b}$ represents a single bond, an alkylene group, an alkenylene group, an alkynylene group, an arylene group, —O—, —S—, —$NR^a$—, a divalent heterocyclic group, an amide bond, an ester bond, a thioester bond, a divalent phosphate group, a phosphanediyl group, a sulfonyl group or a divalent group which is a combination of two or more selected from the group consisting of the aforementioned groups and bonds.

$LL^{1c}$ represents an n2-valent alkane, an n2-valent alkene, an n2-valent alkyne, an n2-valent arene, an n2-valent heterocyclic group, a trivalent phosphate group, a phosphanetriyl group, an isocyanurate group, or an n2-valent group which is a combination of two or more groups and bonds selected from the group consisting of the aforementioned groups, alkylene groups, alkenylene groups, alkynylene groups, arylene groups, —O—, —S—, —$NR^a$—, an ester bond, a thioester bond, an amide bond, a thioamide bond, and a sulfonyl group.

$R^a$ represents a hydrogen atom or a substituent and preferably represents a hydrogen atom.

$Y^4$, $Y^7$, $Y^{10}$, and $Y^{13}$ each represent a hydroxy group or an alkoxy group. $Y^5$, $Y^6$, $Y^8$, $Y^9$, $Y^{11}$, $Y^{12}$, $Y^{14}$, and $Y^{15}$ each represent a hydroxy group, an alkoxy group, an alkyl group, or a ketoxime group.

n2 is 3 or 4.

Note that a partial structure ("—NH—") taken from an amide bond is not interpreted as —$NR^a$— and that a partial structure ("—O—") taken from an ester bond is not interpreted as —O—. Even in the case where an acid anhydride group has a heterocycle, this acid anhydride group is not interpreted as a heterocyclic group.

With regard to the structure corresponding to $LL^{1a}$-$L^2$— in the compound represented by general formula (2), structures are defined in the order of $LL^{1a}$ and $L^2$.

Provided that there is a group that can be interpreted as both a group represented by $LL^{1a}$ and a combination of a group represented by $LL^{1a}$ or the like and a bond represented by $L^2$ (for example, a hydroxy group, a sulfanyl group, a thiocyanato group, an ureido group, an acid anhydride group, a carboxy group, an acyl group, or a carbamoyl group), the group is preferentially interpreted as a group represented by $LL^{1a}$. When $L^2$ is a combination of two or more selected from the group consisting of an alkylene group, an alkenylene group, an alkynylene group, an arylene group, —O—, —S—, —$NR^a$—, an ester bond, a thioester bond, an amide bond, a thioamide bond, and a sulfonyl group, the $L^2$ is interpreted such that the number of groups (bonds) constituting this combination is the smallest.

When Exemplary compound K-5 shown below is explained as an example, $LL^{1a}$ represents an acyl group, and $L^2$ represents a combination of an oxygen atom and an alkylene group. When Exemplary compound K-8 shown below is explained as an example, $LL^{1a}$ represents a sulfanyl group, and $L^2$ represents an alkylene group. When Exemplary compound K-11 shown below is explained as an example, $LL^{1a}$ represents a thiocyanato group, and $L^2$ represents an alkylene group.

With regard to the structure corresponding to -$L^3$-$LL^{1b}$-$L^4$— in the compound represented by general formula (3), structures are defined in the order of $L^3$, $L^4$, and $LL^{1b}$. In this case, $L^3$ and $L^4$ are selected so as to minimize the number of combinations of the groups (bonds) represented by $L^3$ and the number of combinations of the groups (bonds) represented by $L^4$.

When Exemplary compound K-24 shown below is explained as an example, $L^3$ represents an alkylene group, $L^4$ represents an alkylene group, and $LL^{1b}$ represents a combination of an ester bond and —O—. When Exemplary compound K-25 shown below is explained as an example, $L^3$ represents an alkylene group, $L^4$ represents an alkylene group, and $LL^{1b}$ represents a combination of two ester bonds and an alkenylene group.

Provided that the structure corresponding to -$L^3$-$LL^{1b}$-$L^4$- is one type of group (for example, an alkylene group), it is interpreted that $L^3$ and $L^4$ each represent a single bond.

With regard to the structure corresponding to $LL^{1c}$-$(L^5)_{n2}$- in the compound represented by general formula (4), structures are defined in the order of $L^5$ and $LL^{1c}$. In this case, $L^5$ is selected so as to minimize the number of combinations of the group or the like represented by $L^5$.

Provided that the structure corresponding to $LL^{1c}$-$(L^5)_{n2}$- is one type of group (for example, an n2-valent alkane), it is interpreted that $L^5$, the number of which is n2, each represent a single bond.

The alicyclic group that may be employed as $LL^{1a}$ may be any of a cycloalkyl group, a cycloalkenyl group, and a cycloalkynyl group. The number of carbon atoms of the cycloalkyl group is preferably 3 to 20, more preferably 4 to 15, and still more preferably 5 to 10. The number of carbon atoms of the cycloalkenyl group and the number of carbon atoms of the cycloalkynyl group are each preferably 6 to 20, more preferably 6 to 15, more preferably 6 to 10, and still more preferably 6.

The heterocyclic ring constituting the heterocyclic group that may be employed as $LL^{1a}$ may be a saturated or unsaturated aliphatic heterocyclic ring or an aromatic heterocyclic ring and may be a monocycle or a fused ring. The heterocyclic ring may be a bridged ring. Examples of heteroatoms included in the heterocyclic ring include an oxygen atom, a nitrogen atom, and a sulfur atom. The number of heteroatoms included in one heterocyclic ring is not particularly limited but is preferably 1 to 3 and more preferably 1 or 2. The number of carbon atoms of the heterocyclic ring is preferably 2 to 10 and more preferably 4 or 5. The heterocyclic ring is preferably a three- to seven-membered ring, more preferably a three- to six-membered ring, and still more preferably a three- to five-membered ring. Specific examples of the heterocyclic ring include an epoxy group, a 3,4-epoxycyclohexane ring, a furan ring, and a thiophene ring.

The number of carbon atoms of the acyl group that may be employed as $LL^{1a}$ is preferably 0 to 40, more preferably 0 to 30, more preferably 0 to 20, more preferably 0 to 15, and still more preferably 0 to 10. In the present invention, the acyl group includes a formyl group, a carbamoyl group, an alkyl carbonyl group, an alkenyl carbonyl group, and an aryl carbonyl group. Preferred examples of the alkenyl carbonyl group include a (meth)acryloyl group.

The acid anhydride group that may be employed as $LL^{1a}$ is preferably a monovalent group having a carboxylic acid anhydride structure. Examples thereof include a maleic anhydride group, a succinic anhydride group, a glutaric anhydride group, an adipic anhydride group, and a citraconic anhydride group, such as 3,4-dihydro-2,5-furandionyl.

The alkylene group that may be employed as $L^2$ may be linear or branched. The number of carbon atoms of the alkylene group is preferably 1 to 30, more preferably 1 to 25, more preferably 1 to 20, and more preferably 1 to 15. Specific examples of the alkylene group include methylene, ethylene, isopropylene, butylene, pentylene, cyclohexylene, heptylene, octylene, nonylene, decylene, and undecylene.

The alkenylene group that may be employed as $L^2$ may be linear or branched. The number of carbon atoms of the alkenylene group is preferably 2 to 20, more preferably 2 to 15, more preferably 2 to 10, and still more preferably 2 to 6. Specific examples of the alkenylene group include ethenylene and propenylene.

The alkynylene group that may be employed as $L^2$ may be linear or branched. The number of carbon atoms of the alkynylene group is preferably 2 to 20, more preferably 2 to 15, more preferably 2 to 10, and still more preferably 2 to 6. Specific examples of the alkynylene group include ethynylene and propynylene.

The number of carbon atoms of the arylene group that may be employed as $L^2$ is preferably 6 to 20, more preferably 6 to 15, more preferably 6 to 12, and still more preferably 6 to 10. Specific examples of the arylene group include phenylene and naphthylene.

Examples of the substituent in $R^a$ of —$NR^a$— that may be employed as $L^2$ include alkyl groups (preferably having 1 to 12 carbon atoms and more preferably having 1 to 8 carbon atoms), alkenyl groups (preferably having 2 to 12 carbon atoms and more preferably having 2 to 8 carbon atoms), alkynyl groups (preferably having 2 to 12 carbon atoms and more preferably having 2 to 8 carbon atoms), aryl groups (preferably having 6 to 20 carbon atoms and more preferably having 6 to 10 carbon atoms), and heterocyclic groups. Examples of the heterocyclic ring constituting the heterocyclic group that may be employed as $R^a$ include the heterocyclic rings constituting the heterocyclic group that may be employed as $LL^{1a}$. Preferred forms of the heterocyclic group are also the same as the preferred forms of the heterocyclic group that may be employed as $LL^{1a}$.

An example of —$NR^a$— is —NH—.

The number of groups and bonds combined and constituting the divalent group that is a combination of two or more selected from the group consisting of the aforementioned groups and bonds and that may be employed as $L^2$ (hereinafter also referred to as a "group that is a combination and that may be employed as $L^2$") is preferably 2 to 8, more preferably 2 to 6, and still more preferably 2 to 4.

The molecular weight of the group that is a combination and that may be employed as $L^2$ is preferably 20 to 1,000, more preferably 30 to 500, and still more preferably 40 to 200.

Examples of the group that is a combination and that may be employed as $L^2$ include a urea bond, a thiourea bond, a carbamate group, a sulfonamide bond, arylene-alkylene, —O— alkylene, $NR^a$-alkylene, amide bond-alkylene, —S-alkylene, alkylene-O-amide bond-alkylene, alkylene-amide bond-alkylene, alkenylene-amide bond-alkylene, alkylene-ester bond-alkylene, arylene-ester bond-alkylene, -(alkylene-O)—, alkylene-O-(alkylene-O)-alkylene (where "(alkylene-O)" each represent a repeating unit), an arylene-sulfonyl-O-alkylene, and an ester bond-alkylene (where the term "group" is omitted, and a similar description may be made below).

Examples of the alkylene groups, the alkenylene groups, the alkynylene groups, the arylene groups, and —$NR^a$— that may be employed as $L^3$ to $L^5$ include the alkylene groups, the alkenylene groups, the alkynylene groups, the arylene groups, and the —$NR^a$— that may be employed as $L^2$, and preferred forms thereof are also the same as the preferred forms of the alkylene groups, the alkenylene groups, the alkynylene groups, the arylene groups, and —$NR^a$—that may be employed as $L^2$.

The alkylene group that may be employed as $LL^{1b}$ may be linear, branched, or cyclic. The number of carbon atoms of the alkylene group is preferably 1 to 30, more preferably 1 to 25, more preferably 1 to 20, and more preferably 1 to 15. Specific examples of the alkylene group include methylene, ethylene, isopropylene, butylene, pentylene, cyclohexylene, heptylene, octylene, nonylene, decylene, and undecylene.

The alkenylene group that may be employed as $LL^{1b}$ may be linear, branched, or cyclic. The number of carbon atoms of the alkenylene group is preferably 2 to 20, more preferably 2 to 15, more preferably 2 to 10, and still more preferably 2 to 6. Specific examples of the alkenylene group include ethenylene and propenylene.

The alkynylene group that may be employed as $LL^{1b}$ may be linear, branched, or cyclic. The number of carbon atoms of the alkynylene group is preferably 2 to 20, more preferably 2 to 15, more preferably 2 to 10, and still more preferably 2 to 6. Specific examples of the alkynylene group include ethynylene and propynylene.

Examples of the arylene group that may be employed as $LL^{1b}$ include the arylene groups that may be employed as $L^2$ to $L^5$, and preferred forms thereof are also the same as the preferred forms of the arylene group that may be employed as $L^2$ to $L^5$.

Examples of the heterocyclic ring constituting the divalent heterocyclic group that may be employed as $LL^{1b}$ include the heterocyclic rings constituting the heterocyclic group that may be employed as $LL^{1a}$, and preferred forms thereof are also the same as the preferred forms of the heterocyclic group that may be employed as $LL^{1a}$. Examples of —$NR^a$— that may be employed as $LL^{1b}$ include the —$NR^a$— that may be employed as $L^2$, and preferred forms thereof are also the same as the preferred forms of —$NR^a$— that may be employed as $L^2$.

The number of groups and bonds combined and constituting the divalent group that is a combination of two or more selected from the group consisting of the aforementioned groups and bonds and that may be employed as $LL^{1b}$ (hereinafter also referred to as a "group that is a combination and that may be employed as $LL^{1b}$") is preferably 2 to 8, more preferably 2 to 6, and still more preferably 2 to 4.

The molecular weight of the group that is a combination and that may be employed as $LL^{1b}$ is preferably 20 to 1,000, more preferably 30 to 500, and still more preferably 40 to 200.

Examples of the group that is a combination and that may be employed as $LL^{1b}$ include a urea bond, a carbonate group, a sulfonamide bond, a disulfide bond, ester bond-alkenylene-ester bond, -(alkylene-O)—, and —O-(alkylene-O)— (where "(alkylene-O)" each represent a repeating unit).

Among the n2-valent alkanes that may be employed as $LL^{1c}$, a trivalent alkane, that is, an alkanetriyl group preferably has 1 to 20 carbon atoms, more preferably 3 to 15 carbon atoms, more preferably 4 to 12 carbon atoms, and still more preferably 5 to 10 carbon atoms.

Among the n2-valent alkanes that may be employed as $LL^{1c}$, a tetravalent alkane, that is, an alkanetetrayl group preferably has 1 to 20 carbon atoms, more preferably 3 to 15 carbon atoms, more preferably 4 to 12 carbon atoms, and still more preferably 5 to 10 carbon atoms.

Among the n2-valent alkenes that may be employed as $LL^{1c}$, a trivalent alkene, that is, an alkenetriyl group preferably has 2 to 20 carbon atoms, more preferably 3 to 15 carbon atoms, more preferably 4 to 12 carbon atoms, and still more preferably 5 to 10 carbon atoms.

Among the n2-valent alkenes that may be employed as $LL^{1c}$, a tetravalent alkene, that is, an alkenetetrayl group preferably has 2 to 20 carbon atoms, more preferably 3 to 15 carbon atoms, more preferably 4 to 12 carbon atoms, and still more preferably 5 to 10 carbon atoms.

Among the n2-valent alkynes that may be employed as $LL^{1c}$, a trivalent alkyne, that is, an alkynetriyl group preferably has 3 to 20 carbon atoms, more preferably 3 to 15 carbon atoms, more preferably 4 to 12 carbon atoms, and still more preferably 5 to 10 carbon atoms.

Among the n2-valent alkynes that may be employed as $LL^{1c}$, a tetravalent alkyne, that is, an alkynetetrayl group preferably has 3 to 20 carbon atoms, more preferably 3 to 15 carbon atoms, more preferably 4 to 12 carbon atoms, and still more preferably 5 to 10 carbon atoms.

Among the n2-valent arenes that may be employed as $LL^{1c}$, a trivalent arene, that is, an arenetriyl group preferably has 6 to 20 carbon atoms, more preferably 6 to 15 carbon atoms, more preferably 6 to 12 carbon atoms, and still more preferably 6 to 10 carbon atoms. Specific examples of the arenetriyl group include benzenetriyl and naphthalenetriyl.

Among the n2-valent arenes that may be employed as $LL^{1c}$, a tetravalent arene, that is, an arenetetrayl group preferably has 6 to 20 carbon atoms, more preferably 6 to 15 carbon atoms, more preferably 6 to 12 carbon atoms, and still more preferably 6 to 10 carbon atoms. Specific examples of the arenetetrayl group include benzenetetrayl and naphthalenetetrayl.

Examples of the heterocyclic ring constituting the n2-valent heterocyclic group that may be employed as $LL^{1c}$ include the heterocyclic ring constituting the heterocyclic group that may be employed as $LL^{1a}$, and preferred forms thereof are also the same as the preferred forms of the heterocyclic ring that may be employed as $LL^{1a}$. Examples of —$NR^a$— that may be employed as $LL^{1c}$ include the —$NR^a$— that may be employed as $L^2$, and preferred forms thereof are also the same as the preferred forms of the —$NR^a$— that may be employed as $L^2$.

The number of groups and bonds combined and constituting the n2-valent group which is a combination of two or more groups and bonds selected from the group consisting of the aforementioned groups, alkylene groups, alkenylene groups, alkynylene groups, arylene groups, —O—, —S—, —$NR^a$—, an ester bond, a thioester bond, an amide bond, a thioamide bond, and a sulfonyl group that may be employed as $LL^{1c}$ (hereinafter also referred to as a "group that is a combination and that may be employed as $LL^{1c}$") is preferably 2 to 8, more preferably 2 to 6, and still more preferably 2 to 4.

The molecular weight of the group that is a combination and that may be employed as $LL^{1c}$ is preferably 20 to 1,000, more preferably 30 to 500, and still more preferably 40 to 200.

Examples of the group that is a combination and that may be employed as $LL^{1c}$ include a glycerol group, a trimethylolpropyl group, a 1,3,5-triazine group, and an isocyanuric group (1,3,5-triazine-2,4,6(1H,3H,5H)-trione-1,3,5-triyl group).

The alkyl group constituting the alkoxy group that may be employed as $Y^4$ to $Y^{15}$ may be linear, branched, or cyclic and may have these forms in combination. In the present invention, this alkyl group is preferably a linear alkyl group. The number of carbon atoms of the alkyl group constituting the alkoxy group is preferably 1 to 15, more preferably 1 to 10, more preferably 1 to 5, and still more preferably 1 or 2. Specific examples of the alkyl group constituting the alkoxy group include methyl, ethyl, propyl, tert-butyl, pentyl, and cyclohexyl.

Examples of the alkyl groups that may be employed as $Y^5$, $Y^6$, $Y^8$, $Y^9$, $Y^{11}$, $Y^{12}$, $Y^{14}$, and $Y^{15}$ include the alkyl groups constituting the alkoxy groups that may be employed as $Y^4$ to $Y^{15}$, and preferred forms thereof are also the same as the preferred forms of the alkyl groups constituting the alkoxy groups that may be employed as $Y^4$ to $Y^{15}$.

The ketoxime group is a substituent having the following structure.

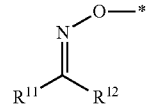

In the above structure, $R^{11}$ and $R^{12}$ each represent a substituent, and * represents a portion bound to a silicon atom.

Examples of the substituent that may be employed as $R^{11}$ and $R^{12}$ include the substituents in the $R^a$, and preferred forms thereof are also the same as the preferred forms of the substituent that may be employed as the $R^a$.

Examples of the ketoxime group include a dimethyl ketoxime group, a methyl ethyl ketoxime group, and a diethyl ketoxime group.

The compound represented by general formula (1) may have a substituent as long as the effects of the present invention are not impaired. Examples of this substituent include the above-described groups that may be employed as $LL^{1a}$, alkyl groups, alkenyl groups, alkynyl groups, and aryl groups. Examples of this substituent further include an unsubstituted silyl group and substituted silyl groups having no alkoxy group or hydroxy group.

In general formula (2), $LL^{1a}$ or $L^2$ and at least one of $Y^5$ or $Y^6$ may be linked to each other to form a ring. The number of atoms constituting this ring is preferably 3 to 10, more preferably 4 to 8, and still more preferably 5 or 6.

In general formula (3), $LL^{1b}$ or $L^3$ and at least one of $Y^8$ or $Y^9$ may be linked to each other to form a ring. The number of atoms constituting this ring is preferably 3 to 10, more preferably 4 to 8, and still more preferably 5 or 6. $LL^{1b}$ or $L^4$ and at least one of $Y^{11}$ or $Y^{12}$ may be linked to each other to form a ring. The number of atoms constituting this ring is preferably 3 to 10, more preferably 4 to 8, and still more preferably 5 or 6. Two or more of these rings may be formed at the same time.

In general formula (4), $LL^{1c}$ or $L^5$ and at least one of $Y^{13}$ or $Y^{14}$ may be linked to each other to form a ring. The number of atoms constituting this ring is preferably 3 to 10, more preferably 4 to 8, and still more preferably 5 or 6.

In general formula (2), $LL^{1a}$ preferably represents a hydrogen atom, an alicyclic group, a heterocyclic group, a hydroxy group, a sulfanyl group, a thiocyanato group, an acid anhydride group, a carboxy group, an acyl group, or a sulfonic group. $L^2$ preferably represents an alkylene group, an alkenylene group, an alkynylene group, an arylene group, —O—, —S—, —NR$^a$—, an ester bond, a thioester bond, an amide bond, a sulfonyl group, or a divalent group which is a combination of two or more selected from the group consisting of the aforementioned groups and bonds.

In general formula (2), $LL^{1a}$ preferably represents a hydrogen atom, a hydroxy group, a carboxylic acid anhydride group, a carboxy group, an acyl group, or a sulfonic group. $L^2$ more preferably represents an alkylene group, an alkenylene group, —O—, —NR$^a$—, an ester bond, an amide bond, or a divalent group which is a combination of two or more selected from the group consisting of the aforementioned groups and bonds.

Specific example of $LL^{1a}$-$L^2$- include hydrogen atom-alkenylene, hydrogen atom-arylene-alkylene, alicyclic-alkylene, heterocyclic-alkylene, acyl-O-alkylene, acyl-NR$^a$-alkylene, sulfanyl-alkylene, heterocyclic-S-alkylene, thiocyanato-alkylene, hydroxy-alkylene, hydroxy-alkylene-amide bond-alkylene, carboxy-alkylene, acyl-alkylene-amide bond-alkylene, acid anhydride-alkylene, hydrogen atom-arylene-ester bond-alkylene, hydrogen atom-alkylene-O-(alkylene-O)-alkylene, sulfonic acid-alkylene, and hydrogen atom-arylene-sulfonyl-O-alkylene.

In general formula (2), at least two of $Y^4$ to $Y^6$ are each preferably an alkoxy group or a hydroxy group, and all of $Y^4$ to $Y^6$ are each more preferably an alkoxy group or a hydroxy group.

In general formula (3), $LL^{1b}$ preferably represents an alkylene group, an alkenylene group, an arylene group, —O—, —S—, an ester bond, a thioester bond, an amide bond, a sulfonyl bond, or a divalent group which is a combination of two or more selected from the group consisting of the aforementioned groups and bonds. $L^3$ and $L^4$ each preferably represent a single bond, an alkylene group, an alkenylene group, an alkynylene group, an arylene group, —O—, —S—, an ester bond, a thioester bond, an amide bond, a sulfonyl group, or a divalent group which is a combination of two or more selected from the group consisting of the aforementioned groups and bonds, and more preferably represent a single bond, an alkylene group, an alkenylene group, —O—, an ester bond, or an amide bond.

Specific examples of -$L^3$-$LL^{1b}$-$L^4$- include alkylene, alkylene-ester bond-O-alkylene, alkylene-ester bond-alkenylene-ester bond-alkylene, alkylene-O-(alkylene-O)-alkylene, alkylene-arylene-alkylene, and alkylene-S—S-alkylene.

In general formula (3), at least two of $Y^7$ to $Y^9$ are each preferably an alkoxy group or a hydroxy group.

In general formula (3), at least two of $Y^{10}$ to $Y^{12}$ are each preferably an alkoxy group or a hydroxy group.

In general formula (4), n2 is preferably 3, and $LL^{1c}$ preferably represents an isocyanurate group. $L^5$ preferably represents an alkylene group.

In general formula (4), at least two of $Y^{13}$ to $Y^{15}$ are each preferably an alkoxy group or a hydroxy group, and all of $Y^{13}$ to $Y^{15}$ are each more preferably an alkoxy group or a hydroxy group.

In general formula (4), n2 is preferably 3.

The compound represented by general formula (1) and used in the present invention contributes to adhesion between the flexible tube base and the resin cover layer in a monomolecular form. The thickness of the primer layer is remarkably smaller than that of a typical adhesive layer (in other words, the concept of the thickness cannot be recalled). That is, the primer layer including the compound represented by general formula (1) differs from such an adhesive layer that requires a certain degree of thickness and softness for adhesion between the flexible tube base and the resin cover layer. Therefore, in fact, the primer layer does not affect the resilience of the flexible tube, and thus the flexible tube according to the present invention also has good resilience.

In the present invention, the expression "a primer layer includes a compound represented by general formula (1)" is meant to include a form in which the compound represented by general formula (1) is included in a state of having reacted with the flexible tube base and a form in which the compound represented by general formula (1) is included in a state of having reacted with the resin cover layer. Specifically, at least a portion of the compound represented by general formula (1) is hydrolyzed and a hydroxy group is thereby exposed, and the compound represented by general formula (1) can be present in a state where the exposed hydroxy group reacts with the metal constituting the flexible tube base or reacts with a group on the surface of the resin cover layer.

Alternatively, for example, when the primer layer is formed by using a coating liquid, the pH of which has been adjusted to be acidic or alkaline as described below, a portion of the compound represented by general formula (1) may be present in the form of a salt or an ion. An example of the form of an ion is a form in which a group capable of forming an anion (anionic group) is present as an anion. An example of the form of a salt is a form in which the anionic group is present as a salt-type group having, as a counter cation, for example, an alkali metal ion such as a sodium ion or a potassium ion.

Specific examples of the compound represented by general formula (1) are shown below, but the present invention is not limited to these examples. In the present invention, when Exemplary compound K-5 below is used, the resin cover layer preferably includes at least one of compound selected from the group consisting of polyamides, polyesters, or polyolefins and more preferably includes a polyamide.

In the structures below, Me represents methyl, and Et represents ethyl. The structure in the parentheses in compound K-20 represents a repeating unit with a number of repetitions of 6 to 9. The structure in the parentheses in compound K-26 represents a repeating unit with a number of repetitions of 6 to 9.

In the chemical structural formulae below, with regard to compounds that represent alkoxy groups as substituents bound to a silicon atom, compounds having structures in which some or all of the alkoxy groups are hydroxy groups are also included in specific examples of the compounds represented by general formula (1).

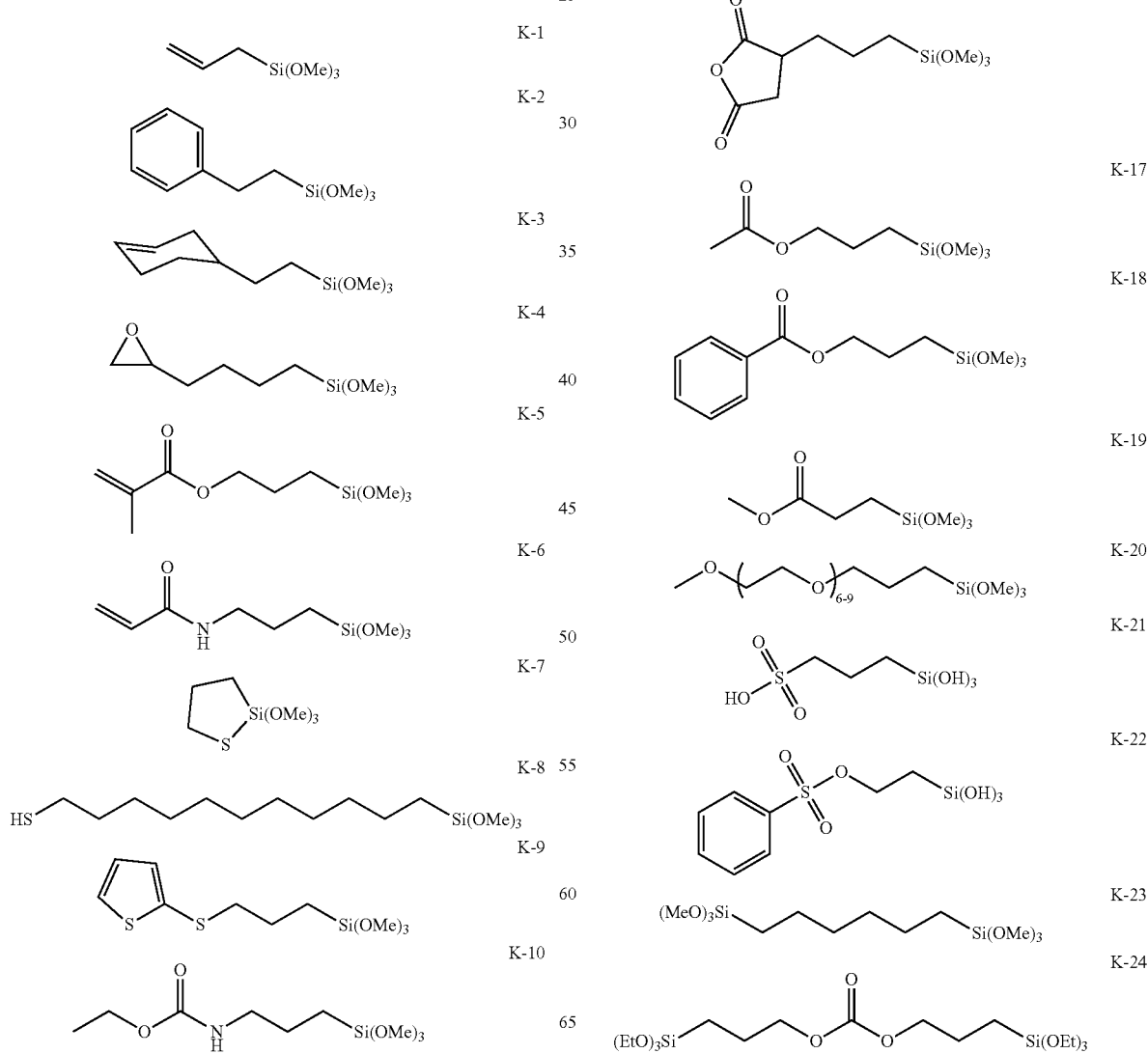

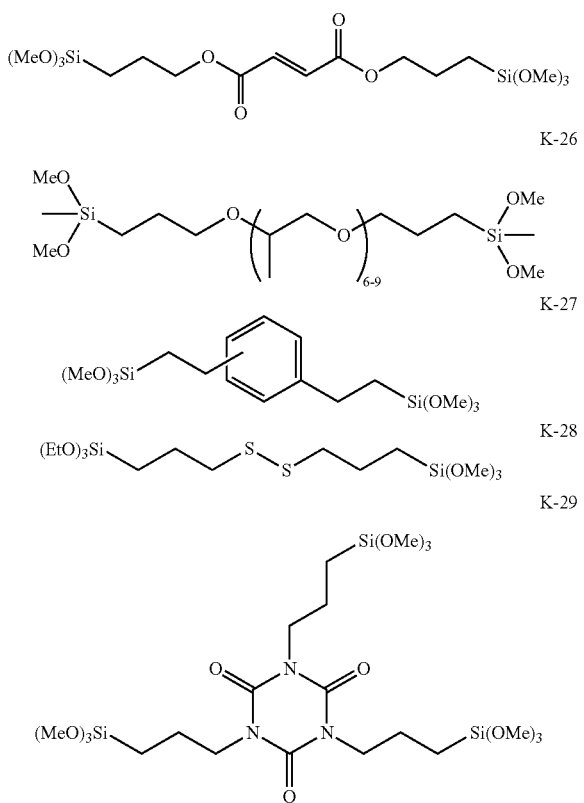

The content of the compound represented by general formula (1) in the primer layer is not particularly limited. However, the lower limit of the content is preferably 90% by mass or more, more preferably 95% by mass or more, still more preferably 97% by mass or more, and particularly preferably 99% by mass or more. The upper limit can be 100% by mass.

The primer layer may contain one or two or more compounds represented by general formula (1). When two or more compounds represented by general formula (1) are contained, the total amount of the compounds contained is defined as the content of the compounds represented by general formula (1) in the primer layer.

The primer layer may contain, besides the compounds represented by general formula (1), additives such as a surfactant, a thickener, a leveling agent, a stabilizer, and an antifoaming agent as long as the effects of the present invention are not impaired.

Resin Cover Layer

The flexible tube according to the present invention has a resin cover layer on an outer periphery of a flexible tube base having a primer layer thereon.

In the embodiment in FIG. 2, an outer surface of a resin cover layer 15 is coated with a topcoat layer 16 that contains fluorine or the like and that contributes to, for example, chemical resistance. In FIG. 2, a spiral tube 11 is illustrated as a single layer. Alternatively, the spiral tube 11 may be formed by concentrically stacking two or more layers. Note that the resin cover layer 15 and the topcoat layer 16 in the figure are shown to be thicker than the actual thicknesses with respect to the diameter of a flexible tube base 14 for the sake of clearly illustrating the layer structure.

In the present invention, the resin cover layer covers an outer peripheral surface of the flexible tube base having the above-described primer layer thereon. The resin cover layer 15 in the embodiment in FIG. 2 has a two-layer structure in which an inner layer 17 that covers the entire peripheral surface around the axis of the flexible tube base 14 and an outer layer 18 that covers the entire peripheral surface around the axis of the inner layer 17 are stacked. Typically, a soft resin is used as the material of the inner layer 17, and a hard resin is used as the material of the outer layer 18. However, the present invention is not limited to these embodiments.

In the present invention, when the resin cover layer has a multilayer structure having two or more layers, at least the innermost layer (layer that is in contact with the primer layer) includes at least one selected from the group consisting of polyamides, polyesters, polyurethanes, and polyolefins, as described below. In the present invention, when the resin cover layer is formed of a single layer, this single-layer resin cover layer includes at least one selected from the group consisting of polyamides, polyesters, polyurethanes, and polyolefins. That is, the resin cover layer in the present invention includes at least one compound selected from the group consisting of polyamides, polyesters, polyurethanes, and polyolefins at least on the side of the resin cover layer in contact with the primer layer.

The at least one compound selected from the group consisting of polyamides, polyesters, polyurethanes, and polyolefins preferably includes at least one compound selected from the group consisting of polyamides, polyesters, and polyurethanes from the viewpoint of further improving adhesiveness by enhancing the interaction between -LL$^1$ and the polymer (compound) constituting the resin cover layer to achieve better bending durability. It is considered that when the resin cover layer contains at least one compound selected from the group consisting of polyamides, polyesters, and polyurethanes, for example, at least any of a hydrogen bond with any of an amide bond, an ester bond, and a urethane bond, a hydrogen bond with a hydroxy residue in polyamides, polyesters, and polyurethanes, a covalent bond with a carboxy residue, an amino residue, or a hydroxy residue in polyamides, polyesters, and polyurethanes, or the like is efficiently produced, and the adhesiveness to the resin cover layer can be further improved.

The polyamides, polyesters, polyurethanes, and polyolefins included in the resin cover layer are preferably thermoplastic.

From the viewpoint of the necessity of forming a resin cover layer having a relatively small thickness by a thermal process, the melt volume rate (MVR) of the thermoplastic polymer is preferably 1 cm$^3$/10 min to 100 cm$^3$/10 min, more preferably 2 cm$^3$/10 min to 80 cm$^3$/10 min, and still more preferably 3 cm$^3$/10 min to 60 cm$^3$/10 min.

The MVR is a value measured in accordance with JIS K 7210-1.

Polyamide

Typical polyamides that can be used as a resin cover layer of a flexible tube for an endoscope can be widely employed as the polyamides. Examples thereof include crystalline polyamides, amorphous polyamides, and polyamide elastomers.

Examples of the crystalline polyamides include, but are not particularly limited to, aliphatic polyamides and aromatic polyamides.

Examples of the aliphatic polyamides include poly-s-caproamide (polyamide 6), polytetramethylene adipamide (polyamide 46), polyhexamethylene adipamide (polyamide 66), polycaproamide/polyhexamethylene adipamide copolymers (polyamide 6/66), polyundecamide (polyamide 11), polycaproamide/polyundecamide copolymers (polyamide 6/11), polydodecamide (polyamide 12), polycaporamide/polydodecamide copolymers (polyamide 6/12), polyhexamethylene sebacamide (polyamide 610), polydecamethylene sebacamide (polyamide 1010), polyhexamethylene dodecamide (polyamide 612), polydecamethylene dodecamide (polyamide 1012), polyundecamethylene adipamide (polyamide 116), and mixtures and copolymers thereof.

Examples of the aromatic polyamides include polyhexamethylene isophthalamide (polyamide 6I), polyhexamethylene terephthalamide (polyamide 6T), polyhexamethylene terephthalamide/polyhexamethylene isophthalamide copolymers (polyamide 6T/6I), polycaproamide/polyhexamethylene terephthalamide copolymers (polyamide 6/6T), polycaproamide/polyhexamethylene isophthalamide copolymers (polyamide 6/6I), polyhexamethylene adipamide/polyhexamethylene terephthalamide copolymers (polyamide 66/6T), polyhexamethylene adipamide/polyhexamethylene isophthalamide copolymers (polyamide 66/6I ), polytrimethylhexamethylene terephthalamide (polyamide TMDT), polybis(4-aminocyclohexyl)methane dodecamide (polyamide PACM12), polybis(3-methyl-4-aminocyclohexyl)methane dodecamide (nylon dimethyl PACM12), poly-m-xylylene adipamide (polyamide MXD6), polydecamethylene terephthalamide (polyamide 10T), polyundecamethylene terephthalamide (polyamide 11T), and mixtures and copolymers thereof.

Examples of the amorphous polyamides include polycondensates of isophthalic acid/terephthalic acid/1,6-hexanediamine/bis(3-methyl-4-aminocyclohexyl)methane, polycondensates of terephthalic acid/2,2,4-trimethyl-1,6-hexanediamine/2,4,4-trimethyl-1,6-hexanediamine, polycondensates of isophthalic acid/bis(3-methyl-4-aminocyclohexyl)methane/ω-laurolactam, polycondensates of isophthalic acid/terephthalic acid/1,6-hexanediamine, polycondensates of isophthalic acid/2,2,4-trimethyl-1,6-hexanediamine/2,4,4-trimethyl-1,6-hexanediamine, polycondensates of isophthalic acid/terephthalic acid/2,2,4-trimethyl-1,6-hexanediamine/2,4,4-trimethyl-1,6-hexanediamine, polycondensates of isophthalic acid/bis(3-methyl-4-aminocyclohexyl)methane/ω-laurolactam, and polycondensates of isophthalic acid/terephthalic acid/other diamine components.

Examples of the polyamide elastomers include elastomers containing polyamides as hard segments, the elastomers being called amide-based thermoplastic elastomers. Examples thereof include multiblock copolymers having hard segments composed of polyamides and soft segments composed of polyethers or polyesters, and multiblock copolymers having hard segments composed of polyamides and soft segments having bonding forms of both an ether bond and an ester bond. Examples of the hard segments include polyamides 6, 66, 610, 11, and 12. Examples of the polyethers for the soft segments include polyethylene glycol, poly(oxytetramethylene) glycol, and poly(oxypropylene) glycol. Examples of the polyesters include poly(ethylene adipate) glycol and poly(butylene-1,4-adipate) glycol.

From the viewpoint of bending durability and durability against strongly acidic liquids, the polyamide used in the present invention is preferably polyamide 1010, polyamide 11, polyamide 12, or a polyamide elastomer.

Examples of commercially available polyamide resins used in the present invention include polyamide 11 (trade name "Rilsan BMN O" manufactured by Arkema Inc.), polyamide 12 (trade name "DAIAMID L1940" manufactured by Daicel-Evonik Ltd.), polyamide 1010 (trade name "VESTAMID Terra DS16" manufactured by Daicel-Evonik Ltd.), polyamide 1012 (trade name "VESTAMID Terra DD16" manufactured by Evonik), an amorphous polyamide (trade name "TROGAMID CX7323" manufactured by Daicel-Evonik Ltd.), and polyamide elastomers (trade name "PEBAX 7233" and "PEBAX Rnew 80R53" manufactured by Arkema Inc.).

These polyamides may be used alone or in combination of two or more thereof.

Polyester

Typical polyesters that can be used as a resin cover layer of a flexible tube for an endoscope can be widely employed as the polyesters. Examples thereof include thermoplastic polyesters and polyester elastomers.

Examples of the thermoplastic polyesters include polyesters formed from a dicarboxylic acid component and a diol component and polyesters formed from a hydroxycarboxylic acid component.

Examples of the dicarboxylic acid component include terephthalic acid, isophthalic acid, phthalic acid, 2,6-naphthalenedicarboxylic acid, 4,4'-biphenyldicarboxylic acid, 5-sodiosulfoisophthalic acid, oxalic acid, succinic acid, adipic acid, sebacic acid, azelaic acid, dodecanedioic acid, dimer acids, maleic anhydride, maleic acid, fumaric acid, itaconic acid, citraconic acid, mesaconic acid, and cyclohexanedicarboxylic acid.

Examples of the diol component include ethylene glycol, diethylene glycol, 1,3-propanediol, 1,4-butanediol, neopentyl glycol, 1,6-hexanediol, cyclohexanedimethanol, triethylene glycol, polyethylene glycol, polypropylene glycol, polytetramethylene glycol, and ethylene oxide adducts of bisphenol A, bisphenol S, and the like.

Examples of the hydroxycarboxylic acid component include s-caprolactone, lactic acid, and 4-hydroxybenzoic acid.

The thermoplastic polyesters may be homopolymers formed from the dicarboxylic acid component and the diol component or homopolymers formed from the hydroxycarboxylic acid component, or copolymers formed from the above components. The thermoplastic polyesters may further contain a small amount of a trifunctional or higher compound component such as trimellitic acid, trimesic acid, pyromellitic acid, trimethylolpropane, glycerol, or pentaerythritol.

Examples of the polyester elastomers include elastomers containing polyesters as hard segments, the elastomers being called ester-based thermoplastic elastomers. Examples thereof include multiblock copolymers having hard segments composed of crystalline polyesters and soft segments composed of polyethers or polyesters, and multiblock copolymers having hard segments composed of crystalline polyesters and soft segments having bonding forms of both an ether bond and an ester bond.

Examples of the hard segments include polybutylene terephthalate and polyethylene terephthalate.

Examples of the soft segments include polyalkylene glycols such as polytetramethylene glycol and polypropylene glycol, bisphenol A-ethylene oxide adducts, bisphenol A-propylene oxide adducts, and polyesters such as polycaprolactone.

For example, block copolymers composed of high-melting-point polyester segments (hard segments) and low-melting-point polymer segments (soft segments) having a molecular weight of 400 to 6,000 can be used, as described in, for example, JP1999-92636A (JP-H11-92636A).

To further improve the bending durability, the thermoplastic polyester used in the present invention preferably has a structure derived from polybutylene naphthalate.

Examples of commercially available polyester resins used in the present invention include polyester elastomers (trade name "PELPRENE P-70B" and "PELPRENE S-3001" manufactured by Toyobo Co., Ltd.) and (trade name "PRIMALLOY B1942" manufactured by Mitsubishi Chemical Corporation) and polybutylene terephthalate (trade name "NOVADURAN 5505S" manufactured by Mitsubishi Engineering-Plastics Corporation).

These polyesters may be used alone or in combination of two or more thereof.

Polyurethane

Typical polyurethanes that can be used as a resin cover layer of a flexible tube for an endoscope can be widely employed as the polyurethanes. For example, carbonate-based, ether-based, or ester-based polyurethanes, or mixed polyurethanes of these can be used. Polyurethane elastomers are also preferred. The polyurethane elastomers may be block polymers including hard segments composed of polyurethanes and soft segments having an ether, ester, or carbonate bond or a mixed form of these bonds, the block polymers being called urethane-based thermoplastic elastomers. Such polyurethane elastomers can be appropriately prepared depending on the purpose. Examples thereof include block polymers including hard segments composed of low-molecular-weight glycol components and diisocyanate components and soft segments composed of high-molecular-weight (long-chain) diol components and diisocyanate components.

Examples of the high-molecular-weight (long-chain) diol components include polyether diols, polyester diols, and lactone-based polyester diols. Examples thereof include polypropylene glycol, polytetramethylene oxide, poly(1,4-butylene adipate), poly(ethylene adipate-co-1,4-butylene adipate), polycaprolactone-based diol, poly(1,6-hexylene carbonate), and poly(1,6-hexylene adipate-co-neopentylene adipate). The high-molecular-weight (long-chain) diols preferably have a number-average molecular weight of 500 to 10,000.

As the low-molecular-weight glycol components, short-chain diols such as ethylene glycol, propylene glycol, 1,4-butanediol, and bisphenol A can be used. The short-chain diols preferably have a number-average molecular weight of 48 to 500.

Examples of the diisocyanate components include diphenylmethane diisocyanate, hexamethylene diisocyanate, tolidine diisocyanate, 1,5-naphthalene diisocyanate, isophorone diisocyanate, and xylylene diisocyanate.

For the polyurethane elastomers according to the above embodiment, disclosure of, for example, JP2005-015643A can be referred to.

Examples of commercially available polyurethanes that can be used in the present invention include PANDEX T-2185 and T-2983N (which are manufactured by DIC Corporation), Miractran (manufactured by Nippon Miractran Co., Ltd.), Elastollan (manufactured by BASF Japan Ltd.), RESAMINE (manufactured by Dainichiseika Color & Chemicals Mfg. Co., Ltd.), Pellethane (manufactured by Dow Chemical Japan Ltd.), Iron Rubber (manufactured by NOK Corporation), and Mobilon (manufactured by Nisshinbo Chemical Inc.). Examples thereof further include Isoplast (manufactured by Lubrizol Corporation), Tecoflex (manufactured by Lubrizol Corporation), Superflex 830, 460, 870, 420, and 420NS (polyurethanes manufactured by DKS Co., Ltd.), Hydran AP-40F, WLS-202, and HW-140SF (polyurethanes manufactured by Dainippon Ink and Chemicals, Inc.), Olester UD500 and UD350 (polyurethanes manufactured by Mitsui Chemicals, Inc.), and Takelac W-615, W-6010, W-6020, W-6061, W-405, W-5030, W-5661, W-512A-6, W-635, and WPB-6601 (manufactured by Mitsui Chemicals, Inc.).

These polyurethanes may be used alone or in combination of two or more thereof.

Polyolefin

Typical polyolefins that can be used as a resin cover layer of a flexible tube for an endoscope can be widely employed as the polyolefins. Examples thereof include polyolefins and olefin-based elastomers.

Examples of the polyolefins include homopolymers and copolymers of α-olefins having 2 to 20 carbon atoms, such as ethylene, propylene, 1-butene, 1-hexene, and 4-methylpentene. Examples thereof further include copolymers of α-olefins and nonconjugated dienes having 2 to 20 carbon atoms, such as dicyclopentadiene, 1,4-hexadiene, cyclooctadiene, methylene norbornene, ethylidene norbornene, butadiene, and isoprene. Examples thereof further include ethylene-α-olefin copolymer rubbers, ethylene-α-olefin-nonconjugated diene copolymer rubbers, propylene-α-olefin copolymer rubbers, and butene-α-olefin copolymer rubbers. It is also possible to use, for example, ethylene-(meth) acrylic acid copolymers, ethylene-(meth)acrylic acid ester-(meth)acrylic acid copolymers, ethylene-vinyl acetate copolymers, ethylene-vinyl acetate-(meth)acrylic acid copolymers, ethylene-propylene-(meth)acrylic acid copolymers, ethylene-propylene-(meth)acrylic acid ester-(meth) acrylic acid copolymers, ethylene-maleic anhydride copolymers, ethylene-(meth)acrylic acid ester-maleic anhydride copolymers, ethylene-butene-maleic anhydride and/or (meth)acrylic acid copolymers, propylene-butene-maleic anhydride and/or (meth)acrylic acid copolymers, and ethylene-vinyl chloride copolymers.

The olefin-based elastomers are elastomers including polyolefins as hard segments and rubber components as soft segments, the elastomers being called olefin-based thermoplastic elastomers. Examples of the olefin elastomers include blend-type elastomers, dynamically crosslinked-type elastomers, and polymer-type elastomers of the above polyolefins and rubber components.

Examples of the polyolefins in the olefin-based elastomers include ethylene-propylene copolymers, ethylene-1-butene copolymers, ethylene-α-olefin copolymers, propylene-1-butene copolymers, propylene-α-olefin copolymers, 1-butene-α-olefin copolymers, propylene-1-butene-ethylene copolymers, propylene-α-olefin-ethylene copolymers, propylene-α-olefin-1-butene copolymers, 1-butene-α-olefin-ethylene copolymers, and polypropylene.

Examples of the rubber components in the olefin-based elastomers include polyisoprene, polybutadiene, polychloroprene, isobutylene-isoprene copolymers, propylene rubber (PP), ethylene-propylene rubber (EPM), and ethylene-propylene-diene rubber (EPDM).

The olefin-based elastomers may contain one of the polyolefins alone or two or more of the polyolefins in combination and may contain one of the rubber components alone or two or more of the rubber components in combination.

Examples of commercially available polyolefins used in the present invention include an olefin-based elastomer (trade name "SARLINK 3145D" manufactured by Toyobo Co., Ltd.).

These polyolefins may be used alone or in combination of two or more thereof.

The total amount of polymers selected from the group consisting of polyamides, polyesters, polyurethanes, and polyolefins contained in the resin cover layer in the case of a single-layer resin cover layer, and the total amount of polymers selected from the group consisting of polyamides, polyesters, polyurethanes, and polyolefins contained in the innermost layer in the case of a multilayer resin cover layer are each preferably 50% by mass or more, more preferably 70% by mass or more, still more preferably 80% by mass or more, and still more preferably 90% by mass or more. When the resin cover layer is formed of a single layer, the resin cover layer may be a layer composed of at least one selected from the group consisting of polyamides, polyesters, polyurethanes, and polyolefins. When the resin cover layer is formed of a plurality of layers, the innermost layer may be a layer composed of at least one selected from the group consisting of polyamides, polyesters, polyurethanes, and polyolefins.

When the resin cover layer in the case of a single-layer resin cover layer and the innermost layer in the case of a multilayer resin cover layer include a polymer other than polyamides, polyesters, polyurethanes, and polyolefins, the polymer is not particularly limited as long as the effects of the present invention are not impaired. Examples of the polymer other than polyamides, polyesters, polyurethanes, and polyolefins include polystyrene and polycarbonate.

The resin cover layer may contain various common additives as long as the effects of the present invention are not impaired. Examples of the additives include a heat-resistant stabilizer, a mineral filler, an impact resistance-improving agent, a plasticizer, a lubricant, a metal soap, a light-fast auxiliary agent, and a colorant. The contents of the additives in the resin cover layer can also be appropriately adjusted. Such additives may be derived from resin materials used or can be added separately from polymers.

When the resin cover layer is formed of a plurality of layers, a layer other than the innermost layer preferably includes at least one selected from the group consisting of polyurethane elastomers, polyamide elastomers, and polyester elastomers. A layer having desired physical properties can be formed by appropriately combining these resins. When the resin cover layer is formed of a plurality of layers, the layer other than the innermost layer more preferably includes a polyurethane elastomer or an alloy of a polyurethane elastomer and a polyester elastomer from the viewpoint of further enhancing the resilience.

Each of the polymers that can be used as the resin cover layer according to the present invention preferably has a molecular weight of 10,000 to 1,000,000, more preferably has a molecular weight of 20,000 to 500,000, and particularly preferably has a molecular weight of 30,000 to 300,000.

In the present invention, the molecular weight of the polymer means a weight-average molecular weight unless otherwise noted. The weight-average molecular weight can be measured by GPC as a molecular weight in terms of polystyrene.

As illustrated in FIG. 2, the resin cover layer 15 in the present invention is preferably formed so as to have a substantially uniform thickness in the longitudinal direction (axial direction) of the flexible tube base 14. The resin cover layer 15 has a thickness of, for example, 0.2 mm to 1.0 mm. An outer diameter D of the flexible tube 3a is appropriately determined according to the purpose and is, for example, 11 to 14 mm. In FIG. 2, the inner layer 17 and the outer layer 18 are formed such that a proportion of a thickness of the inner layer 17 to a total thickness of the resin cover layer 15 and a proportion of a thickness of the outer layer 18 to the total thickness of the resin cover layer 15 change in the axial direction of the flexible tube base 14. Specifically, on one end 14a side (distal end side) of the flexible tube base 14 to be attached to the angle portion 3b, the thickness of the inner layer 17 is larger than the thickness of the outer layer 18 with respect to the total thickness of the resin cover layer 15. The thickness of the inner layer 17 gradually decreases from the one end 14a toward the other end 14b side (proximal end side) to be attached to the main body operating section 5. On the other end 14b side, the thickness of the outer layer 18 is larger than the thickness of the inner layer 17.

In FIG. 2, the proportion of the thickness of the inner layer 17 is the maximum at the one end 14a, and the proportion of the thickness of the outer layer 18 is the maximum at the other end 14b. A ratio of the thickness of the inner layer 17 to the thickness of the outer layer 18 (thickness of inner layer 17:thickness of outer layer 18) can be, for example, 9:1 at the one end 14a, and, for example, 1:9 at the other end 14b. The thicknesses of the two layers are changed such that the ratio of the thickness of the inner layer 17 to the thickness of the outer layer 18 is reversed from the one end 14a to the other end 14b. With this configuration, the flexible tube 3a has a difference in hardness between the one end 14a side and the other end 14b side, and flexibility can be changed in the axial direction such that the one end 14a side is soft and the other end 14b side is hard. The inner layer and the outer layer are preferably formed such that the thickness ratio at the one end is 95:5 to 60:40 (inner layer:outer layer) and the thickness ratio at the other end is 5:95 to 40:60 (inner layer:outer layer).

When the ratio of the thickness of the inner layer 17 to the thickness of the outer layer 18 is within the range of 5:95 to 95:5, the amount of extrusion of a resin that forms a layer having a smaller thickness can also be accurately controlled.

The soft resin used in the inner layer 17 and the hard resin used in the outer layer 18 preferably satisfy the following relations. A difference in 100% modulus, which is an indicator indicating a hardness after molding, is preferably 1 MPa or more and more preferably 3 MPa or more. A difference in melt viscosity at a molding temperature of 150° C. to 300° C., which is an indicator indicating the fluidity of a resin in a molten state, is preferably 2,500 Pas or less. With this configuration, the resin cover layer 15 formed of the inner layer 17 and the outer layer 18 reliably achieves both good molding accuracy and the necessary difference in hardness between the distal end side and the proximal end side.

Topcoat Layer

In the flexible tube according to the present invention, the topcoat layer 16 is disposed on an outer periphery of the resin cover layer 15 as needed. Examples of the material of the topcoat layer include, but are not particularly limited to, urethane coatings, acrylic coatings, fluorine coatings, silicone coatings, epoxy coatings, and polyester coatings.

Main purposes of use of the topcoat layer are to protect the surface of the flexible tube, to make the surface of the flexible tube glossy, to impart slidability, and to impart chemical resistance. Therefore, the topcoat layer is preferably formed of a material that has a high modulus of elasticity, that provides a smooth surface, and that has good chemical resistance.

Method for Producing Flexible Tube

Formation of Primer Layer

In the production of a flexible tube according to the present invention, first, a primer layer is formed on an outer periphery of a flexible tube base. The primer layer can be formed by dissolving a compound represented by general formula (1) above in a solvent to prepare a coating liquid; forming a coating film on at least the outer periphery of the flexible tube base by, for example, applying or spraying the coating liquid onto the outer periphery of the flexible tube base or immersing the flexible tube base in the coating liquid; and subsequently drying the coating film by an ordinary method (for example, high-temperature drying at 100° C. to 170° C.).

Examples of the solvent that can be used for the coating liquid include alcohol solvents such as methanol and ethanol; ketone solvents such as acetone and methyl ethyl ketone; ester solvents such as ethyl acetate; hydrocarbon solvents such as toluene; and liquid mixtures thereof. It is preferable to mix water with the solvents in order to accelerate hydrolysis of an alkoxy group bound to the silicon atom in the compound represented by general formula (1). The pH of the coating liquid is not particularly limited but may be adjusted as required to be acidic (for example, pH 1 to 4 at 25° C.) or alkaline (for example, pH 9 to 11 at 25° C.) by using a pH adjuster, for example.

The content of the compound represented by general formula (1) in the coating liquid is not particularly limited, can be, for example, 0.01% by mass to 2% by mass, and is preferably 0.05% by mass or more and less than 1.5% by mass and more preferably 0.1% by mass or more and less than 1.0% by mass.

The coating liquid may include, for example, a surfactant and a catalyst besides the compound represented by general formula (1), the solvent, and the pH adjuster. The coating liquid is more preferably constituted by the compound represented by general formula (1) and the solvent.

In the present invention, a portion that is not covered with the primer layer may be present on the outer periphery of the flexible tube base as long as the effects of the present invention are not impaired (that is, a defect may be partially generated in the primer layer).

Prior to the formation of the primer layer, the flexible tube base is preferably cleaned by degreasing with an alkali solution, an aqueous solution of a surfactant, an organic solvent, or the like. After the cleaning, the flexible tube base is preferably further washed with water or hot water. After the washing with water or hot water, the flexible tube base is preferably dried (for example, at 100° C. for 10 minutes).

Formation of Resin Cover Layer

The production of the flexible tube for an endoscope according to the present invention includes a step of forming a resin cover layer. The step of forming a resin cover layer includes covering, with a resin that includes at least one compound selected from the group consisting of polyamides, polyesters, polyurethanes, and polyolefins, the primer layer formed on the outer periphery of the flexible tube base so as to be in contact with the primer layer.

The formation of the resin cover layer will be described using, as an example, a case where the resin cover layer has a two-layer structure.

A flexible tube including a resin cover layer that has a two-layer structure having an inner layer and an outer layer can be produced by, for example, melt-kneading and extruding, around the flexible tube base on which the primer layer has been formed, a first resin material (resin material including at least one compound selected from the group consisting of polyamides, polyesters, polyurethanes, and polyolefins) that forms the inner layer and a second resin material that forms the outer layer, thereby covering the flexible tube base.

In an embodiment in which a resin cover layer is formed of one layer or three or more layers, the resin cover layer can also be produced by appropriately changing the layer structure with reference to the method described below.

Figure 3:
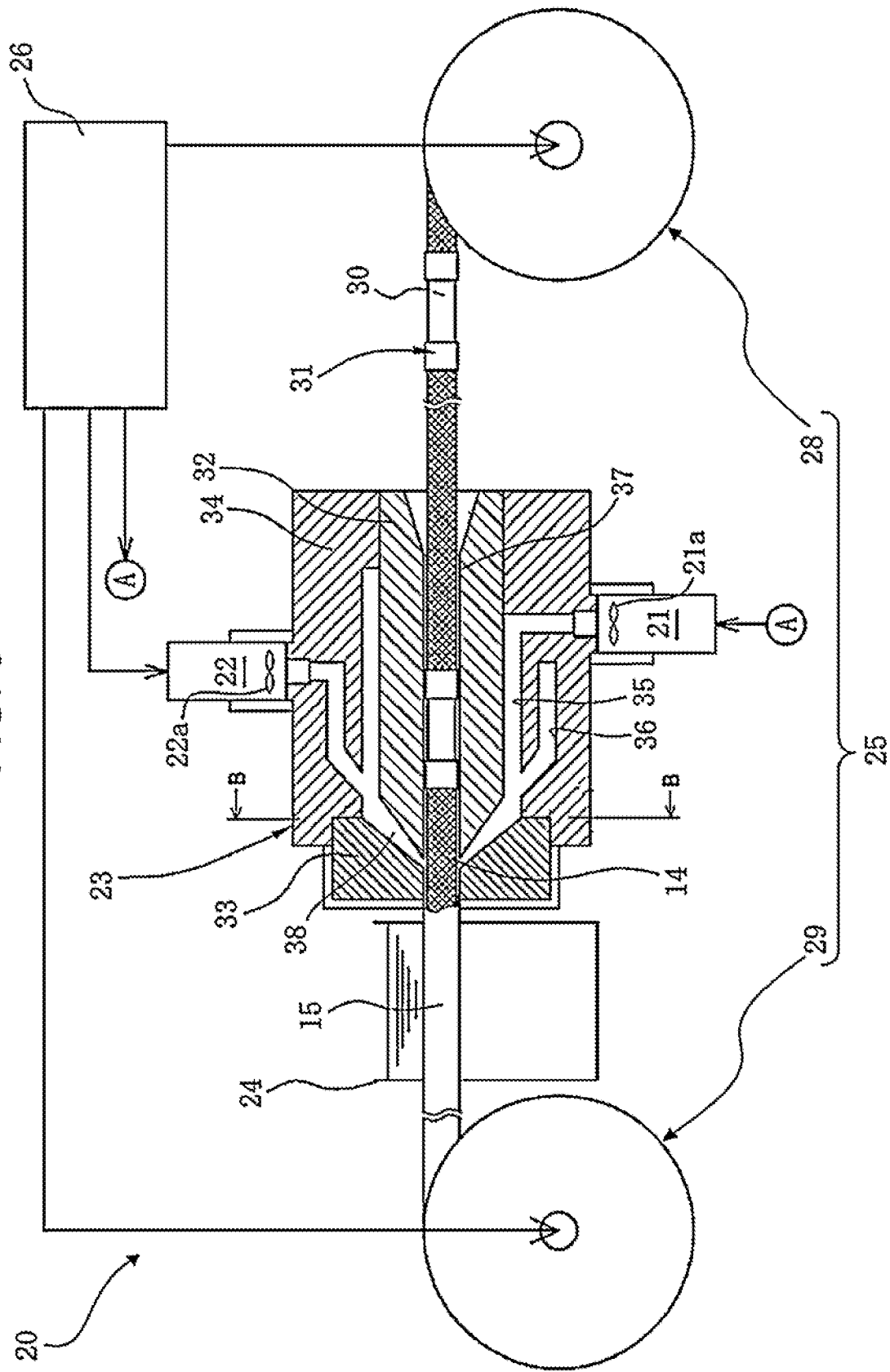
FIG. 3 is a block diagram illustrating a configuration of an apparatus for producing a flexible tube for an endoscope according to an embodiment.
Figure 4:
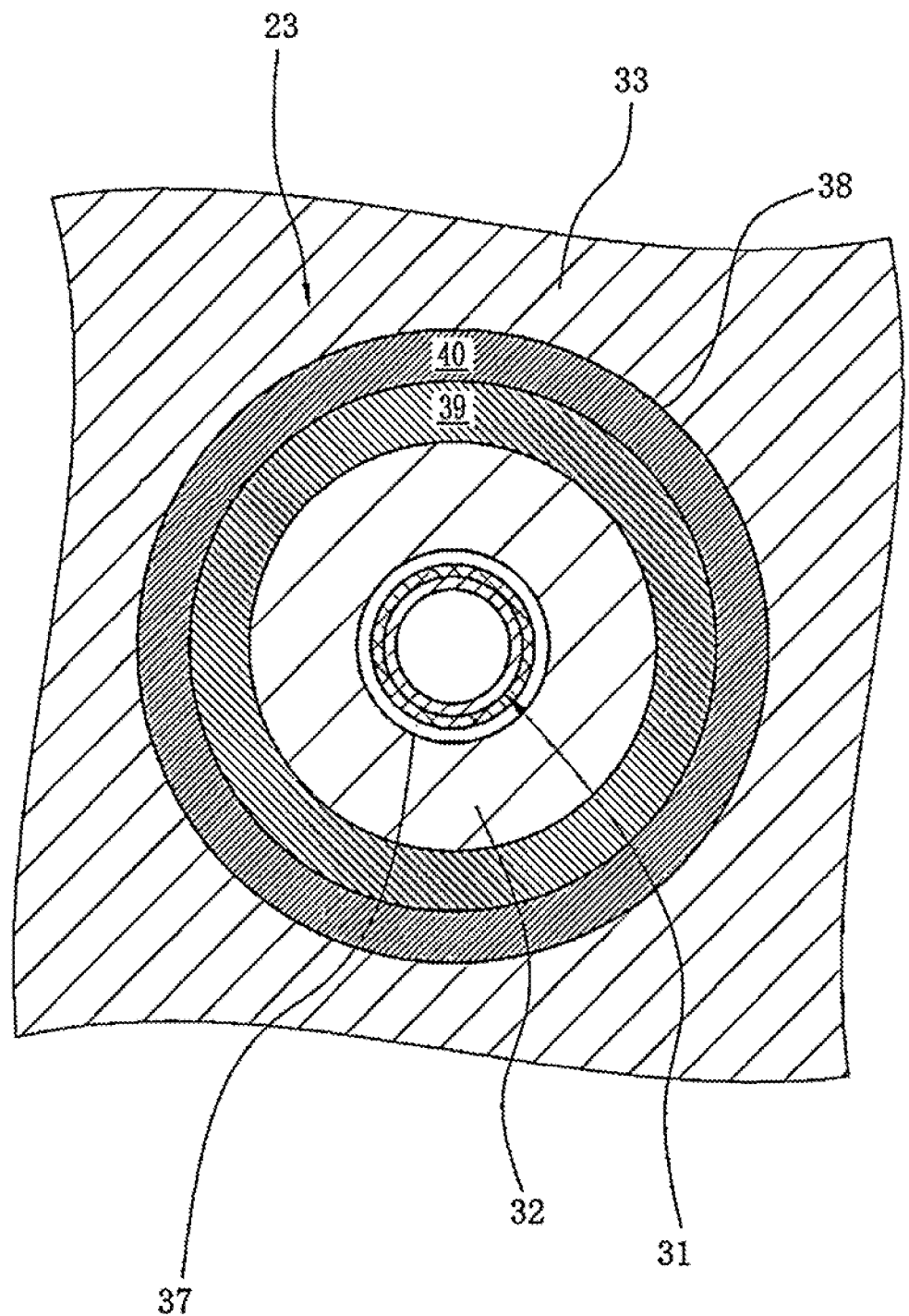
FIG. 4 is a sectional view taken along line B-B in FIG. 3.

An example of a method for forming a resin cover layer of the flexible tube 3a (FIGS. 1 and 2) will be described with reference to FIGS. 3 and 4. In this embodiment, a continuous molding machine is used for molding a resin cover layer 15. It is preferable to use a continuous molding machine 20 that includes well-known extrusion units 21 and 22 including hoppers, screws 21a and 22a, etc.; a head unit 23 configured to mold a resin cover layer 15 so as to cover an outer peripheral surface of a flexible tube base 14; a cooling unit 24; a transport unit 25 (including a supply drum 28 and a take-up drum 29) configured to transport a connected flexible tube base 31 to the head unit 23; and a control unit 26 configured to control the above units. The head unit 23 preferably includes a nipple 32, a die 33, and a support 34 configured to support the nipple 32 and the die 33 in a fixed manner. For example, the apparatus disclosed in FIGS. 3 to 5 of JP2011-72391A can be used as an example of the apparatus having the above configuration.

The inside of the die 33 is preferably heated to a predetermined molding temperature.

The molding temperature is preferably set in a range of 150° C. to 300° C. By controlling a temperature of a heating unit in the apparatus by heating, temperatures of a first resin material (soft resin) 39 and a second resin material (hard resin) 40 can be increased. In addition to this, as the rotation speeds of the screws 21a and 22a increase, the temperatures of the first resin material 39 and the second resin material 40 can be further increased to enhance the fluidity of the respective resin materials. In this case, the molding thicknesses of an inner layer 17 and an outer layer 18 can be respectively adjusted by changing the amounts of ejection of the first resin material 39 and the second resin material 40 in the molten state, while a transport speed of the connected flexible tube base 31 is made constant.

A process of molding the resin cover layer 15 on the connected flexible tube base 31 by the continuous molding machine 20 will be described. When the continuous molding machine 20 performs a molding process, the first resin material 39 and the second resin material 40 in the molten state are extruded from the extrusion units 21 and 22, respectively, to the head unit 23. Furthermore, the transport unit 25 operates so that the connected flexible tube base 31 is transported to the head unit 23. At this time, the extrusion units 21 and 22 are in a state of constantly extruding the first resin material 39 and the second resin material 40, respectively, to supply the resin materials 39 and 40 to the head unit 23, and the first resin material 39 and the second resin material 40 that are respectively extruded from the extrusion units 21 and 22 to gates 35 and 36 pass through edges and join to each other, and are supplied, in a stacked state, through a resin passage 38 to a molding passage 37. As a result, a two-layer molded resin cover layer 15 is formed in which an inner layer 17 composed of the first resin material 39 and an outer layer 18 composed of the second resin material 40 are stacked.

The connected flexible tube base 31 includes a plurality of flexible tube bases 14 (each having a primer layer on the outer periphery thereof) that are connected together. While the connected flexible tube base 31 is transferred in the molding passage 37, the resin cover layer 15 is continuously molded on the plurality of flexible tube bases 14. When the resin cover layer 15 is molded from one end 14a side (distal end side) of one flexible tube base to the other end 14b side (proximal end side) thereof, the thickness of the inner layer 17 is controlled to be large immediately after the extrusion units 21 and 22 start ejection of the resins. The proportion of the outer layer 18 is then gradually increased in an intermediate portion toward the other end 14b side. In this manner, the amounts of the resins ejected are preferably controlled such that the resin cover layer 15 has the thickness ratio that changes in a gradient manner.

Joint members 30 each function as a connecting portion of two flexible tube bases 14, and thus the joint members 30 are used for switching the amounts of resins ejected from the extrusion units 21 and 22 by the control unit 26. Specifically, the control unit 26 preferably switches the amounts of resins ejected from the extrusion units 21 and 22 such that the thickness ratio changes from a thickness ratio on the other end 14b side (proximal end side) of one flexible tube base 14 to a thickness ratio on one end 14a side (distal end side) of a next flexible tube base 14. When the resin cover layer 15 is molded from the one end 14a side of the next flexible tube base 14 to the other end 14b side thereof, the extrusion units 21 and 22 are preferably similarly controlled such that the thickness of the outer layer gradually increases from the one end side toward the other end side.

The connected flexible tube base 31 on which the resin cover layer 15 has been molded to the rearmost end is removed from the continuous molding machine 20. Subsequently, the joint members 30 are detached from the flexible tube bases 14 to separate the connected flexible tube base 31 into the individual flexible tube bases 14. Next, for each of the separated flexible tube bases 14, the resin cover layer 15 is coated with a topcoat layer 16 to complete flexible tubes 3a. The completed flexible tubes 3a are transferred to an assembly process of an electronic endoscope.

In the present invention, when the resin cover layer is formed of formed of a plurality of layers, a functional layer may be disposed between layers that form the plurality of layers.

An electronic endoscope configured to observe an image of the condition of a subject captured by using an imaging device has been described with reference to the drawings by way of an example. However, the present invention is not limited thereto and is also applicable to an endoscope configured to examine the condition of a subject by employing an optical image guide.

The flexible tube according to the present invention is widely applicable to endoscopic medical devices. For example, the flexible tube according to the present invention is applicable to an endoscope equipped with a clip or a wire at the distal end thereof or to an instrument equipped with a basket or a brush. Note that the term "endoscopic medical device" is meant to broadly include, besides the above-described medical devices that include an endoscope as a basic structure, medical devices and diagnosis and treatment devices that include an insertion section having flexibility and that are introduced into the body and used, such as remote-controlled medical devices.

An endoscopic medical device according to the present invention includes the flexible tube for an endoscope according to the present invention, the flexible tube being incorporated in an insertion section of the endoscopic medical device. That is, a method for producing an endoscopic medical device according to the present invention includes incorporating the flexible tube for an endoscope according to the present invention into an insertion section of an endoscopic medical device.

EXAMPLES

Hereafter, the present invention will be described in more detail by way of Examples. However, it is to be understood that the present invention is not limited to these Examples.

Examples and Comparative Examples

Production of Flexible Tube for Endoscope

Flexible tubes having the structure illustrated in FIG. 2 were produced. The resin cover layers had a single-layer structure as shown in tables below.

Flexible Tube Base

Flexible tube bases were prepared. Each of the flexible tube bases had a form in which a spiral tube 11 was formed by using a metal strip 11a made of stainless steel, and the spiral tube 11 was covered with a tubular mesh 12 obtained by weaving stainless steel fibers. The flexible tube base has a length of 80 cm and a diameter of 12 mm. This stainless steel flexible tube base has a passivation layer on a surface thereof, the passivation layer being formed by annealing treatment (heating treatment) in the formation of the spiral tube and the tubular mesh.

Preparation of Coating Liquid for Forming Primer Layer

A solution having a ratio water/ethanol of 5/75 on a mass basis was prepared. Each of the compounds shown in the tables below was separately dissolved in the solution so as to have a concentration of 5.0 g/kg. The resulting solutions were used as coating liquids for forming primer layers.

Formation of Primer Layer

The flexible tube bases were cleaned by immersing in a 7.5% aqueous solution of sodium hydroxide at 60° C. for one minute (degreasing/cleaning step). Subsequently, the flexible tube bases were rinsed with distilled water and then dried in an oven at 100° C. for 10 minutes. The cleaned flexible tube bases were immersed in the above-prepared coating liquids for forming primer layers at room temperature for one minute and then dried in an oven at 160° C. for 10 minutes. Thus, flexible tube bases each having a primer layer on the outer periphery thereof (the surface to be covered with a resin) were prepared.

Formation of Resin Cover Layer

The outer peripheries of the flexible tube bases having the primer layer thereon were covered with the resins shown in the tables below by extrusion (molding temperature: 200° C.) to produce flexible tubes for endoscopes, the flexible tubes having a resin cover layer. The resin cover layer had a thickness of 0.4 mm.

Evaluation

Bending durability and hydrochloric acid durability of each of the above-produced flexible tubes for endoscopes were evaluated as described in Test Examples below. The results are summarized in the tables below.

Test Example 1

Evaluation of Bending Durability

The above-produced flexible tube (length: 80 cm) for an endoscope was brought into contact, in a U shape, with a semicircular portion of a pulley with a diameter of 10 cm and reciprocated by alternately pulling one end and the other end of the U-shaped flexible tube for an endoscope. This reciprocating motion was performed such that a portion of the flexible tube for an endoscope, the portion having a length of 44. 3 cm and excluding portions each having a length of 17.85 cm from both ends of the flexible tube, successively formed the apex of the U shape while being in contact with the pulley. The number of reciprocating motions in which a crease, floating, tearing, or separation of a resin occurred was evaluated in accordance with the evaluation criteria described below. In this test, "C" or higher is satisfactory.

Evaluation Criteria for Bending Durability
AA: 15,000 times or more
A: 10,000 times or more and less than 15,000 times
B: 1,000 times or more and less than 10,000 times
C: 100 times or more and less than 1,000 times
D: less than 100 times Test Example 2

Evaluation of Hydrochloric Acid Durability

Both ends of the above-produced flexible tube for an endoscope were capped with Teflon (registered trademark) plugs, and the flexible tube was immersed in a 0.5% aqueous hydrochloric acid solution at 23° C. for 150 hours. After the immersion, the surface was sufficiently washed with water to prepare a flexible tube for an endoscope after immersion in the aqueous hydrochloric acid solution. For each of the flexible tube for an endoscope before immersion (flexible tube for an endoscope, the flexible tube not being subjected to immersion) and the flexible tube for an endoscope after immersion, a peeling test was conducted as describe below to measure a 90° peel strength $PS_B$ before immersion and a 90° peel strength $PS_A$ after immersion. A ratio $\{(PS_A/PS_B) \times 100\}$ of the 90° peel strength $PS_A$ after immersion to the 90° peel strength $PS_B$ before immersion was determined, and an evaluation was performed in accordance with the criteria described below. In this test, "C" or higher is satisfactory.

Peeling Test

For the resin cover layer of the flexible tube for an endoscope, a cut having a length of 5 cm and a width of 1 cm and extending in the axial direction of the flexible tube was formed in a direction perpendicular to the resin cover layer such that the cut reached the flexible tube base. For one end of this cut, a cut was further formed in the width direction to form a holding portion for the peeing test. The length direction of the cut formed above is the same as the axial direction of the flexible tube, and the cut has a width of 1 cm on the outer peripheral surface of the resin cover layer. A 90° peel strength between the flexible tube base and the resin cover layer was measured by holding the end of the above-formed cut with a width of 1 cm and peeling off the resin cover layer in the axial direction of the flexible tube at a constant speed while the angle between the flexible tube base and the peeled resin cover layer was maintained at 90°. The peel strength is a value measured with a force gauge and is expressed in units of N/cm. For all the flexible tubes, the 90° peel strength was measured under the same conditions.

Evaluation Criteria for Hydrochloric Acid Durability
AA: 90% or more
A: 80% or more and less than 90%
B: 60% or more and less than 80%
C: 40% or more and less than 60%
D: less than 40%

TABLE 1-1

|  |  |  | Example 1 | Example 2 | Example 3 | Example 4 | Example 5 | Example 6 | Example 7 | Example 8 | Example 9 | Example 10 |
|---|---|---|---|---|---|---|---|---|---|---|---|---|
| Structure | Compound of primer layer | Symbol | K-1 | K-2 | K-3 | K-4 | K-5 | K-6 | K-7 | K-8 | K-9 | K-10 |
|  |  | Abbreviation | Allyl | Phenethyl | Cyclohexenyl | Epoxy | Acryl | Acrylamide | Cyclic sulfur | Mercapto | Thiopene | Carbamate |
|  | Resin cover layer |  | PA1 | PA1 | PA1 | PA1 | PA1 | PA1 | PA1 | PA1 | PA1 | PA1 |
| Evaluation | Bending durability |  | B | B | B | B | A | B | C | C | B | A |
|  | Hydrochloric acid durability |  | A | B | B | C | B | A | C | B | C | B |

|  |  |  | Example 11 | Example 12 | Example 13 | Example 14 | Example 15 | Example 16 | Example 17 | Example 18 | Example 19 | Example 20 |
|---|---|---|---|---|---|---|---|---|---|---|---|---|
| Structure | Compound of primer layer | Symbol | K-11 | K-12 | K-13 | K-14 | K-15 | K-16 | K-17 | K-18 | K-19 | K-20 |
|  |  | Abbreviation | Thiocyanato | Hydroxy 1 | Hydroxy 2 | Carboxylic acid 1 | Carboxylic acid 2 | Anhydride | Acetoxy | Benzoyloxy | Carbomethoxy | PEG |
|  | Resin cover layer |  | PA1 | PA1 | PA1 | PA1 | PA1 | PA1 | PA1 | PA1 | PA1 | PA1 |
| Evaluation | Bending durability |  | C | A | A | A | A | A | B | A | A | A |
|  | Hydrochloric acid durability |  | B | B | B | B | B | B | A | B | B | B |

|  |  |  | Example 21 | Example 22 | Example 23 | Example 24 | Example 25 | Example 26 | Example 27 | Example 28 | Example 29 | Example 30 |
|---|---|---|---|---|---|---|---|---|---|---|---|---|
| Structure | Compound of primer layer | Symbol | K-21 | K-22 | K-23 | K-24 | K-25 | K-26 | K-27 | K-28 | K-29 | K-23 |
|  |  | Abbreviation | Sulfonic acid 1 | Sulfonic acid 1 | Dimer 1 | Dimer 2 | Dimer 3 | Dimer 4 | Dimer 5 | Dimer 6 | Trimer | Dimer 1 |
|  | Resin cover layer |  | PA1 | PA1 | PA1 | PA1 | PA1 | PA1 | PA1 | PA1 | PA1 | PA2 |
| Evaluation | Bending durability |  | A | B | A | A | A | AA | A | A | AA | AA |
|  | Hydrochloric acid durability |  | B | B | AA | AA | AA | A | AA | AA | AA | A |

|  |  |  | Example 31 | Example 32 | Example 33 | Example 34 | Example 35 | Example 36 | Example 37 | Example 38 | Example 39 | Example 40 |
|---|---|---|---|---|---|---|---|---|---|---|---|---|
| Structure | Compound of primer layer | Symbol | K-23 | K-23 | K-3 | K-7 | K-15 | K-16 | K-18 | K-23 | K-29 | K-23 |
|  |  | Abbreviation | Dimer 1 | Dimer 1 | Cyclohexane | Cyclic sulfur | Carboxylic acid 2 | Anhydride | Benzoyloxy | Dimer 1 | Trimer | Dimer 1 |
|  | Resin cover layer |  | PA3 | PA4 | TPEE1 | TPEE1 | TPEE1 | TPEE1 | TPEE1 | TPEE1 | TPEE1 | TPEE2 |

TABLE 1-1-continued

| | | | | | | | | | | | |
|---|---|---|---|---|---|---|---|---|---|---|---|
| Evaluation | Bending durability | A | A | B | C | A | A | B | A | AA | A |
| | Hydrochloric acid durability | AA | AA | B | C | B | B | A | AA | AA | AA |

TABLE 1-2

| | | | Example 41 | Example 24 | Example 43 | Example 44 | Example 45 | Example 46 | Example 47 |
|---|---|---|---|---|---|---|---|---|---|---|
| Structure | Compound of primer layer | Symbol Abbreviation | K-23 Dimer 1 | K-23 Dimer 1 | K-11 Thiocyanato | K-12 Hydroxy 1 | K-15 Carboxylic acid 2 | K-16 Anhydride | K-18 Benzoyloxy |
| | Resin cover layer | | TPEE3 | TPEE4 | TPU1 | TPU1 | TPU1 | TPU1 | TPU1 |
| Evaluation | Bending durability | | A | A | C | A | A | A | B |
| | Hydrochloric acid durability | | AA | AA | B | B | B | B | A |

| | | | Example 48 | Example 49 | Example 50 | Example 51 | Example 52 | Example 53 | Comparative Example 1 |
|---|---|---|---|---|---|---|---|---|---|---|
| Structure | Compound of primer layer | Symbol Abbreviation | K-20 PEG | K-23 Dimer 1 | K-29 Trimer | K-3 Cyclohexane | K-7 Cyclic sulfur | K-29 Trimer | — |
| | Resin cover layer | | TPU1 | TPU1 | TPU1 | PO1 | PO1 | PO1 | PA1 |
| Evaluation | Bending durability | | A | A | AA | B | C | AA | D |
| | Hydrochloric acid durability | | B | AA | AA | B | C | AA | D |

| | | | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|
| Structure | Compound of primer layer | Symbol Abbreviation | — | — | — | R-1 TEOS | R-1 TEOS | R-1 TEOS | R-1 TEOS |
| | Resin cover layer | | TPEE1 | TPU1 | PO1 | PA1 | TPEE1 | TPU1 | PO1 |
| Evaluation | Bending durability | | D | D | D | C | C | D | D |
| | Hydrochloric acid durability | | D | D | D | D | D | D | C |

Note in Tables
Cover Layer Resin
(1) Polyamide
PA1: DAIAMID L1940 (trade name, manufactured by Daicel-Evonik Ltd., polyamide 12, MVR=8 cm³/10 min)
PA2: VESTAMID Terra DS16 (trade name, manufactured by Daicel-Evonik Ltd., polyamide 1010, MVR=20 cm³/10 min)
PA3: Rilsan BMN O (trade name, manufactured by Arkema Inc., polyamide 11, MVR=36 cm³/10 min)
PA4: PEBAX 7233 (trade name, manufactured by Arkema Inc., polyether block amide, MVR=4 cm³/10 min)
(2) Polyester
TPEE1: PELPRENE P-70B (trade name, manufactured by Toyobo Co., Ltd., MVR=20 cm³/10 min)
TPEE2: PELPRENE S-3001 (trade name, manufactured by Toyobo Co., Ltd., MVR=16 cm³/10 min)
TPEE3: PRIMALLOY B1942 (trade name, manufactured by Mitsubishi Chemical Corporation, MVR=59 cm³/10 min)
TPEE4: NOVADURAN 5505S (trade name, manufactured by Mitsubishi Engineering-Plastics Corporation, MVR=25 cm³/10 min)
(3) Polyurethane
TPU1: Miractran E675 (trade name, manufactured by Nippon Miractran Co., Ltd.)
(4) Polyolefin
PO1: SARLINK 3145D (trade name, manufactured by Toyobo Co., Ltd., MVR=54 cm³/10 min)

Compound in Primer Layer
Compound Represented by General Formula (2)
K-1: Allyltrimethoxysilane (manufactured by Gelest, Inc., trade name "SIA0540.0")
K-2: Phenethyltrimethoxysilane (manufactured by Gelest, Inc., trade name "SIP6722.6") K-3: [2-(3-Cyclohexenyl)ethyl]trimethoxysilane (manufactured by Gelest, Inc., trade name "SIC2460.0")
K-4: 5,6-Epoxyhexyltriethoxysilane (manufactured by Gelest, Inc., trade name "SIE4675.0")
K-5: (3-Methacryloxypropyl)trimethoxysilane (manufactured by Gelest, Inc., trade name "SIM6487.4")
K-6: 3-Acrylamidopropyltrimethoxysilane (manufactured by Gelest, Inc., trade name "SIA0146.0")
K-7: 2,2-Dimethoxy-1-thia-2-silacyclopentane (manufactured by Gelest, Inc., trade name "SID3545.0")
K-8: 11-Mercaptoundecyltrimethoxysilane (manufactured by Gelest, Inc., trade name "SIM6480.0")
K-9: 2-(3-Trimethoxysilylpropylthio)thiophene (manufactured by Gelest, Inc., trade name "SIT8411.0")
K-10: Triethoxysilylpropyl ethylcarbamate (manufactured by Gelest, Inc., trade name "SIT8188.0")
K-11: 3-Thiocyanatopropyltriethoxysilane (manufactured by Gelest, Inc., trade name "SIT7908.0")
K-12: Hydroxymethyltriethoxysilane (manufactured by Gelest, Inc., trade name "SIH6175.0") K-13: N-(3-Triethoxysilylpropyl)-4-hydroxybutyramide (manufactured by Gelest, Inc., trade name "SIT8189.5")
K-14: Carboxyethylsilanetriol, disodium salt (manufactured by Gelest, Inc., trade name "SIC2263.0")

K-15: Triethoxysilylpropylmaleamic acid (manufactured by Gelest, Inc., trade name "SIT8189.8")

K-16: (3-Trimethoxysilyl)propyl succinic anhydride (manufactured by Shin-Etsu Chemical Co., Ltd., trade name "X-12-967C")

K-17: 3-Acetoxypropyltrimethoxysilane (manufactured by Gelest, Inc., trade name "SIA0100.0")

K-18: Benzoyloxypropyltrimethoxysilane (manufactured by Gelest, Inc., trade name "SIB0959.0")

K-19: 2-(Carbomethoxy)ethyltrimethoxysilane (manufactured by Gelest, Inc., trade name "SIC2072.0")

K-20: Trimethoxysilylpropoxypolyethyleneoxide, methyl ether (manufactured by Gelest, Inc., trade name "SIT8408.0")

K-21: 3-(Trihydroxysilyl)-1-propanesulfonic acid (manufactured by Gelest, Inc., trade name "SIT8378.3")

K-22: Trihydroxysilylethyl phenylsulphonic acid (manufactured by Gelest, Inc., trade name "SIT8378.1")

Compound Represented by General Formula (3)

K-23: 1,6-Bis(trimethoxysilyl)hexane (manufactured by Gelest, Inc., trade name "SIB1832.0") K-24: Bis(3-triethoxysilylpropyl)carbonate (manufactured by Gelest, Inc., trade name "SIB1824.56")

K-25: Bis(3-trimethoxysilylpropyl)fumarate (manufactured by Gelest, Inc., trade name "SIB1834.5")

K-26: Bis[(3-methyldimethoxysilyl)propyl]polypropylene oxide (manufactured by Gelest, Inc., trade name "SIB1660.0", mass average molecular weight: 700)

K-27: Bis(trimethoxysilylethyl)benzene (manufactured by Gelest, Inc., trade name "SIB1831.0")

K-28: Bis[3-(triethoxysilyl)propyl]disulfide (manufactured by Gelest, Inc., trade name "SIB1824.6")

Compound Represented by General Formula (4)

K-29: Tris(3-trimethoxysilylpropyl)isocyanurate (manufactured by Shin-Etsu Chemical Co., Ltd., trade name "KBM-9659").

Compound Used in Comparative Examples

R-1: Tetraethoxysilane (reagent manufactured by Tokyo Chemical Industry Co., Ltd., trade name "78-10-4")

As shown in Table 1, each of the flexible tubes for endoscopes of Comparative Examples 1 to 4, in which the outer periphery of the flexible tube base was covered with a resin cover layer specified in the present invention without providing a primer layer, was poor in both properties of bending durability and hydrochloric acid durability. The flexible tubes for endoscopes of Comparative Examples 5 to 8 each have a primer layer containing tetraethoxysilane, which is not included in general formula (1), between the flexible tube base and a resin cover layer specified in the present invention. The flexible tubes for endoscopes of Comparative Examples 5 to 8 were each poor in at least one property of bending durability or hydrochloric acid durability, although the results depended on the type of resin included in the resin cover layer.

It was found that, in contrast, each of the flexible tubes for endoscopes of Examples 1 to 53, in which a primer layer contained a compound represented by general formula (1), and a resin cover layer in contact with the primer layer had a resin including at least one selected from the group consisting of polyamides, polyesters, polyurethanes, and polyolefins, could sufficiently maintain the adhesiveness between the flexible tube base and the resin cover layer even when a bending operation was repeated or when the flexible tube was immersed in a 0.5% aqueous hydrochloric acid solution at 23° C. for 150 hours.

The present invention has been described together with embodiments thereof. However, we do not intend to limit our invention in any of the details of the description unless otherwise specified. We believe that the invention should be broadly construed without departing from the spirit and scope of the invention as defined by the appended claims.

REFERENCE SIGNS LIST 2 electronic endoscope (endoscope)
3 insertion section
  3a flexible tube
  3b angle portion
  3c tip portion
5 main body operating section
6 universal cord
11 spiral tube
  11a metal strip
12 tubular mesh
13 cap
14 flexible tube base
  14a distal end side
  14b proximal end side
15 resin cover layer
16 topcoat layer
17 inner layer
18 outer layer
X angle portion 3b side (soft)
Y main body operating section 5 side (hard)
20 continuous molding machine (production apparatus)
21, 22 extrusion unit
  21a screw
  22a screw
23 head unit
24 cooling unit
25 transport unit
26 control unit
28 supply drum
29 take-up drum
30 joint member
31 connected flexible tube base
32 nipple
33 die
34 support
35, 36 gate
37 molding passage
38 resin passage
39 soft resin
40 hard resin

What is claimed is:

1. A flexible tube for an endoscope, the flexible tube comprising:
  a flexible tube base containing metal as a constituent material;
  a resin cover layer that covers an outer periphery of the flexible tube base; and
  a primer layer that includes a compound represented by general formula (1) and that is disposed between the flexible tube base and the resin cover layer,
  wherein the resin cover layer includes at least one compound selected from the group consisting of polyamides, polyesters, polyurethanes, and polyolefins at least on a side of the resin cover layer in contact with the primer layer:

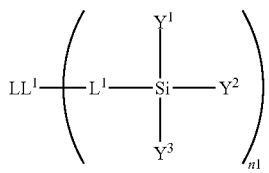

General formula (1)

where $LL^1$ represents a monovalent substituent or an n1-valent linking group, $L^1$ represents a single bond or a divalent linking group, $Y^1$ to $Y^3$ each represent a substituent, and n1 is an integer of 1 to 4, at least one of $Y^1$, $Y^2$, or $Y^3$ is a group selected from the group consisting of alkoxy groups and a hydroxy group, and when n1 is 1, none of $LL^1$-$L^1$ and $Y^1$ to $Y^3$ is a group selected from the group consisting of alkoxy groups and a hydroxy group.

2. The flexible tube for an endoscope according to claim 1, wherein the compound represented by general formula (1) is a compound represented by any one of general formulae (2) to (4):

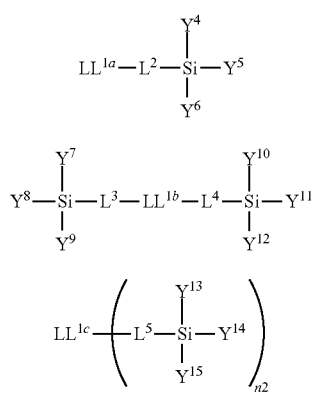

General formula (2)

General formula (3)

General formula (4)

where $LL^{1a}$ represents a hydrogen atom, an alicyclic group, a heterocyclic group, a hydroxy group, a sulfanyl group, an isocyanato group, a thiocyanato group, an ureido group, a cyano group, an acid anhydride group, an azide group, a carboxy group, an acyl group, a thiocarbamoyl group, a phosphate group, a phosphanyl group, a sulfonic group, or a sulfamoyl group;

$L^2$ represents a single bond, an alkylene group, an alkenylene group, an alkynylene group, an arylene group, —O—, —S—, —NR$^a$—, an ester bond, a thioester bond, an amide bond, a thioamide bond, a sulfonyl group, or a divalent group which is a combination of two or more selected from the group consisting of the aforementioned groups and bonds;

$L^3$ to $L^5$ each represent a single bond, an alkylene group, an alkenylene group, an alkynylene group, an arylene group, —O—, —S—, —NR$^a$—, an ester bond, a thioester bond, an amide bond, a thioamide bond, a urea bond, a thiourea bond, a sulfonyl group, a sulfonamide bond, or a divalent group which is a combination of two or more selected from the group consisting of the aforementioned groups and bonds;

$LL^{1b}$ represents a single bond, an alkylene group, an alkenylene group, an alkynylene group, an arylene group, —O—, —S—, —NR$^a$—, a divalent heterocyclic group, an amide bond, an ester bond, a thioester bond, a divalent phosphate group, a phosphanediyl group, a sulfonyl group, or a divalent group which is a combination of two or more selected from the group consisting of the aforementioned groups and bonds;

$LL^{1c}$ represents an n2-valent alkane, an n2-valent alkene, an n2-valent alkyne, an n2-valent arene, an n2-valent heterocyclic group, a trivalent phosphate group, a phosphanetriyl group, an isocyanurate group, or an n2-valent group which is a combination of two or more groups and bonds selected from the group consisting of the aforementioned groups, alkylene a thioester bond, an amide bond, a thioamide bond, and a sulfonyl group;

$R^a$ represents a hydrogen atom or a substituent;

$Y^4$, $Y^7$, $Y^{10}$, and $Y^{13}$ each represent a hydroxy group or an alkoxy group;

$Y^5$, $Y^6$, $Y^8$, $Y^9$, $Y^{11}$, $Y^{12}$, $Y^{14}$, and $Y^{15}$ each represent a hydroxy group, an alkoxy group, an alkyl group, or a ketoxime group; and n2 is 3 or 4.

3. The flexible tube for an endoscope according to claim 2, wherein, in general formula (2), $LL^{1a}$ represents a hydrogen atom, an alicyclic group, a heterocyclic group, a hydroxy group, a sulfanyl group, a thiocyanato group, an acid anhydride group, a carboxy group, an acyl group, or a sulfonic group, and $L^2$ represents an alkylene group, an alkenylene group, an alkynylene group, an arylene group, —O—, —S—, —NR$^a$—, an ester bond, a thioester bond, an amide bond, a sulfonyl group, or a divalent group which is a combination of two or more selected from the group consisting of the aforementioned groups and bonds.

4. The flexible tube for an endoscope according to claim 2, wherein, in general formula (2), $LL^{1a}$ represents a hydrogen atom, a hydroxy group, a carboxylic acid anhydride group, a carboxy group, an acyl group, or a sulfonic group, and $L^2$ represents an alkylene group, an alkenylene group, —O—, —NR$^a$—, an ester bond, an amide bond, or a divalent group which is a combination of two or more selected from the group consisting of the aforementioned groups and bonds.

5. The flexible tube for an endoscope according to claim 2, wherein, in general formula (3), $LL^{1b}$ represents an alkylene group, an alkenylene group, an arylene group, —O—, —S—, an ester bond, a thioester bond, an amide bond, a sulfonyl bond, or a divalent group which is a combination of two or more selected from the group consisting of the aforementioned groups and bonds, and $L^3$ and $L^4$ each represent a single bond, an alkylene group, an alkenylene group, an alkynylene group, an arylene group, —O—, —S—, an ester bond, a thioester bond, an amide bond, a sulfonyl group, or a divalent group which is a combination of two or more selected from the group consisting of the aforementioned groups and bonds.

6. The flexible tube for an endoscope according to claim 2, wherein, in general formula (3), $LL^{1b}$ represents an alkylene group, an alkenylene group, an arylene group, —O—, —S—, an ester bond, a thioester bond, an amide bond, a sulfonyl bond, or a divalent group which is a combination of two or more selected from the group consisting of the aforementioned groups and bonds, and $L^3$ and $L^4$ each represent a single bond, an alkylene group, an alkenylene group, —O—, an ester bond, or an amide bond.

7. The flexible tube for an endoscope according to claim 2, wherein, in general formula (4), n2 is 3, $LL^{1c}$ represents an isocyanurate group, and $L^5$ represents an alkylene group.

8. The flexible tube for an endoscope according to claim 1, wherein the metal that constitutes the flexible tube base is stainless steel.

9. The flexible tube for an endoscope according to claim 1, wherein the metal that constitutes the flexible tube base has a passivation film on a surface thereof.

10. The flexible tube for an endoscope according to claim 1, wherein the resin cover layer has a single-layer structure or a multilayer structure and includes at least one compound selected from the group consisting of polyamides, polyesters, polyurethanes, and polyolefins in a layer in contact with the primer layer.

11. The flexible tube for an endoscope according to claim 1, wherein the resin cover layer includes at least one compound selected from the group consisting of polyamides, polyesters, and polyurethanes at least on the side of the resin cover layer in contact with the primer layer.

12. The flexible tube for an endoscope according to claim 1,
wherein the resin cover layer has a two-layer structure, and
a ratio of a thickness of an inner layer to a thickness of an outer layer of the two-layer structure changes in a gradient manner in an axial direction of the flexible tube base.

13. The flexible tube for an endoscope according to claim 12, wherein the ratio of the thickness of the inner layer to the thickness of the outer layer is inner layer:outer layer=95:5 to 60:40 at one end of the flexible tube for an endoscope and is inner layer:outer layer=5:95 to 40:60 at the other end.

14. An endoscopic medical device comprising the flexible tube for an endoscope according to claim 1.

15. A method for producing a flexible tube for an endoscope, the method comprising:
a step of forming, on at least an outer periphery of a flexible tube base that contains metal as a constituent material, a primer layer that includes a compound represented by general formula (1); and
a step of forming a resin cover layer by covering, with a resin that includes at least one compound selected from the group consisting of polyamides, polyesters, polyurethanes, and polyolefins, the primer layer formed on the outer periphery of the flexible tube base so that the resin cover layer is in contact with the primer layer:

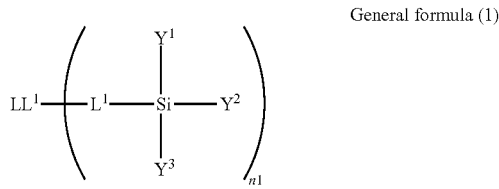

General formula (1)

wherein $LL^1$ represents a monovalent substituent or an n1-valent linking group, $L^1$ represents a single bond or a divalent linking group, $Y^1$ to $Y^3$ each represent a substituent, and n1 is an integer of 1 to 4,
at least one of $Y^1$, $Y^2$, or $Y^3$ is a group selected from the group consisting of alkoxy groups and a hydroxy group, and when n1 is 1, none of $LL^1$-$L^1$ and $Y^1$ to $Y^3$ is a group selected from the group consisting of alkoxy groups and a hydroxy group.

16. The method for producing a flexible tube for an endoscope according to claim 15,
wherein the resin cover layer has a two-layer structure,
at least an inner layer of the two-layer structure includes at least one compound selected from the group consisting of polyamides, polyesters, polyurethanes, and polyolefins, and
a ratio of a thickness of the inner layer to a thickness of an outer layer of the two-layer structure changes in a gradient manner in an axial direction of the flexible tube base.

17. A method for producing an endoscopic medical device, comprising:
a step of producing a flexible tube for an endoscope by the method for producing a flexible tube for an endoscope according to claim 15; and
a step of incorporating the produced flexible tube for an endoscope into an insertion section of an endoscopic medical device.

18. A method for producing an endoscopic medical device, comprising incorporating the flexible tube for an endoscope according to claim 1 into an insertion section of an endoscopic medical device.

* * * * *